United States Patent [19]

Kubota et al.

[11] Patent Number: 5,556,781

[45] Date of Patent: Sep. 17, 1996

[54] DNA ENCODING ENZYME, RECOMBINANT DNA AND ENZYME, TRANSFORMANT, AND THEIR PREPARATIONS AND USES

[75] Inventors: Michio Kubota, Osaka; Keiji Tsusaki, Okayama; Kazuko Hattori, Okayama; Toshiyuki Sugimoto, Okayama, all of Japan

[73] Assignee: Kabushiki Kaisha Hayashibara Seibutsu Kagaku Kenkyujo, Okayama, Japan

[21] Appl. No.: 399,646

[22] Filed: Mar. 7, 1995

[30] Foreign Application Priority Data

Mar. 7, 1994 [JP] Japan .................................... 5-59834
Mar. 7, 1994 [JP] Japan .................................... 5-59840

[51] Int. Cl.$^6$ .................. C12N 9/24; C12N 1/20; C12N 15/00; C07H 21/04
[52] U.S. Cl. .................. 435/200; 435/252.3; 435/320.1; 536/23.2
[58] Field of Search .................. 435/200, 252.3, 435/320.1; 536/23.2

[56] References Cited

U.S. PATENT DOCUMENTS

| 4,521,252 | 6/1985 | Miyake et al. ................ 127/46.3 |
| 5,455,168 | 10/1995 | Maruta et al. ................ 435/201 |
| 5,472,863 | 12/1995 | Maruta et al. ................ 435/200 |

FOREIGN PATENT DOCUMENTS

| 0154485 | 12/1975 | Japan . |
| 0023799 | 2/1983 | Japan . |
| 0072598 | 4/1983 | Japan . |
| 0216695 | 12/1983 | Japan . |
| 2106912 | 4/1983 | United Kingdom . |

OTHER PUBLICATIONS

E. M. Southern, *Detection of Specific Sequences Among DNA Fragments Separated by Gel Electrophoresis*, J. Mol. Biol., vol. 98, pp. 503–517, 1975.

*Enzyme Kinetics of Amylases and Related Enzymes*, Handbook of Amylases and Related Enzymes, pp. 1–9, 1988.

U. K. Laemmli, *Cleavage of Structural Proteins During the Assembly of the Head of Bacteriophage T4*, Nature, vol. 227, pp. 680–685, 15 Aug. 1970.

J. Sambrook et al, *Molecular Cloning a Laboratory Manual*, Second Edition, published by Cold Spring Harbor Laboratory Press, 1989.

Sinnott (1990) Chemical Reviews 90(7): 1171–1202.

*Primary Examiner*—Robert A. Wax
*Assistant Examiner*—Lisa J. Hobbs
*Attorney, Agent, or Firm*—Browdy and Neimark

[57] ABSTRACT

Disclosed are a DNA encoding an enzyme which releases trehalose from non-reducing saccharides having a trehalose structure as an end unit and having a degree of glucose polymerization of 3 or higher, recombinant DNA and enzyme, transformant, and their preparations and uses. These facilitate the industrial-scale production of trehalose with a relative easiness and low cost, and trehalose thus obtained can be satisfactorily used in a variety of food products, cosmetics and pharmaceuticals.

26 Claims, 9 Drawing Sheets

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 1767 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..1767

( x i ) SEQUENCE DESCRIPTION: SEQ ID NO:1:

```
GCC  AAG  CCG  GTG  CAG  GGA  GCG  GGG  CGC  TTC  GAT  ATC  TGG  GCG  CCC  GAG        4 8
Ala  Lys  Pro  Val  Gln  Gly  Ala  Gly  Arg  Phe  Asp  Ile  Trp  Ala  Pro  Glu
 1                    5                        1 0                      1 5

GCA  GGC  ACC  GTA  ACG  CTG  CTG  GCC  GGC  GGG  GAG  CGC  TAC  GAG  ATG  GGC        9 6
```

| | | | | | | | | | | | | | | | | |
|---|---|---|---|---|---|---|---|---|---|---|---|---|---|---|---|---|
| Ala | Gly | Thr | Val | Thr | Leu | Leu | Ala | Gly | Gly | Glu | Arg | Tyr | Glu | Met | Gly | |
| | | | 20 | | | | | 25 | | | | | 30 | | | |
| CGC | CGC | CCC | GGC | AAC | GGG | CCG | GCG | GAC | GAA | GGC | TGG | TGG | ACG | GCC | GCG | 144 |
| Arg | Arg | Pro | Gly | Asn | Gly | Pro | Ala | Asp | Glu | Gly | Trp | Trp | Thr | Ala | Ala | |
| | | 35 | | | | 40 | | | | | 45 | | | | | |
| GAT | GCA | CCG | ACA | GGC | GCG | GAC | GTG | GAC | TAC | GGA | TAC | CTG | CTC | GAC | GGC | 192 |
| Asp | Ala | Pro | Thr | Gly | Ala | Asp | Val | Asp | Tyr | Gly | Tyr | Leu | Leu | Asp | Gly | |
| | 50 | | | | 55 | | | | | 60 | | | | | | |
| GAC | GAA | ATC | CCG | CTG | CCG | GAC | CCC | CGG | ACC | CGC | CGC | CAG | CCC | GAA | GGC | 240 |
| Asp | Glu | Ile | Pro | Leu | Pro | Asp | Pro | Arg | Thr | Arg | Arg | Gln | Pro | Glu | Gly | |
| 65 | | | | 70 | | | | | 75 | | | | | 80 | | |
| GTC | CAT | GCC | CTG | TCC | CGG | ACC | TTC | GAC | CCC | GGC | GCC | CAC | CGC | TGG | CAG | 288 |
| Val | His | Ala | Leu | Ser | Arg | Thr | Phe | Asp | Pro | Gly | Ala | His | Arg | Trp | Gln | |
| | | | | 85 | | | | | 90 | | | | | 95 | | |
| GAC | GCC | GGG | TGG | CAG | GGC | AGG | GAA | CTC | CAG | GGC | TCC | GTG | ATT | TAC | GAA | 336 |
| Asp | Ala | Gly | Trp | Gln | Gly | Arg | Glu | Leu | Gln | Gly | Ser | Val | Ile | Tyr | Glu | |
| | | | 100 | | | | | 105 | | | | | 110 | | | |
| CTC | CAC | ATC | GGA | ACG | TTC | ACG | CCG | GAA | GGG | ACG | CTG | GAC | GCC | GCC | GCG | 384 |
| Leu | His | Ile | Gly | Thr | Phe | Thr | Pro | Glu | Gly | Thr | Leu | Asp | Ala | Ala | Ala | |
| | | 115 | | | | | 120 | | | | | 125 | | | | |
| GGC | AAG | CTG | GAC | TAC | CTC | GCC | GGC | CTG | GGC | ATC | GAC | TTC | ATT | GAG | CTG | 432 |
| Gly | Lys | Leu | Asp | Tyr | Leu | Ala | Gly | Leu | Gly | Ile | Asp | Phe | Ile | Glu | Leu | |
| | 130 | | | | | 135 | | | | | 140 | | | | | |
| CTG | CCC | GTG | AAT | GCC | TTC | AAC | GGC | ACG | CAC | AAC | TGG | GGC | TAC | GAC | GGC | 480 |
| Leu | Pro | Val | Asn | Ala | Phe | Asn | Gly | Thr | His | Asn | Trp | Gly | Tyr | Asp | Gly | |
| 145 | | | | | 150 | | | | | 155 | | | | | 160 | |
| GTC | CAG | TGG | TTT | GCC | GTG | CAT | GAA | GGC | TAC | GGC | GGG | CCT | GCG | GCG | TAC | 528 |
| Val | Gln | Trp | Phe | Ala | Val | His | Glu | Gly | Tyr | Gly | Gly | Pro | Ala | Ala | Tyr | |
| | | | | 165 | | | | | 170 | | | | | 175 | | |
| CAG | CGG | TTC | GTG | GAT | GCG | GCC | CAC | GCG | GCC | GGC | CTC | GGC | GTC | ATC | CAG | 576 |
| Gln | Arg | Phe | Val | Asp | Ala | Ala | His | Ala | Ala | Gly | Leu | Gly | Val | Ile | Gln | |
| | | | 180 | | | | | 185 | | | | | 190 | | | |
| GAC | GTG | GTC | TAC | AAC | CAC | CTC | GGG | CCG | AGC | GGG | AAC | TAC | CTC | CCC | AGG | 624 |
| Asp | Val | Val | Tyr | Asn | His | Leu | Gly | Pro | Ser | Gly | Asn | Tyr | Leu | Pro | Arg | |
| | | 195 | | | | | 200 | | | | | 205 | | | | |
| TAC | GGC | CCG | TAC | CTC | AAG | CAC | GGC | GAA | GGC | AAC | ACC | TGG | GGC | GAT | TCG | 672 |
| Tyr | Gly | Pro | Tyr | Leu | Lys | His | Gly | Glu | Gly | Asn | Thr | Trp | Gly | Asp | Ser | |
| | 210 | | | | | 215 | | | | | 220 | | | | | |
| GTC | AAC | CTG | GAC | GGG | CCG | GGA | TCC | GAC | CAC | GTC | CGC | CAG | TAC | ATC | CTG | 720 |
| Val | Asn | Leu | Asp | Gly | Pro | Gly | Ser | Asp | His | Val | Arg | Gln | Tyr | Ile | Leu | |
| 225 | | | | | 230 | | | | | 235 | | | | | 240 | |
| GAC | AAC | GTG | GCC | ATG | TGG | CTG | CGC | GAC | TAC | CGG | GTG | GAC | GGC | CTC | CGC | 768 |
| Asp | Asn | Val | Ala | Met | Trp | Leu | Arg | Asp | Tyr | Arg | Val | Asp | Gly | Leu | Arg | |
| | | | | 245 | | | | | 250 | | | | | 255 | | |
| CTG | GAC | GCC | GTC | CAC | GCC | CTG | AAG | GAT | GAG | CGG | GCC | GTC | CAC | ATC | CTG | 816 |
| Leu | Asp | Ala | Val | His | Ala | Leu | Lys | Asp | Glu | Arg | Ala | Val | His | Ile | Leu | |
| | | | 260 | | | | | 265 | | | | | 270 | | | |
| GAG | GAG | TTC | GGC | GCG | CTG | GCG | GAC | GCC | CTG | TCG | TCC | GAA | GGC | GGC | CGC | 864 |
| Glu | Glu | Phe | Gly | Ala | Leu | Ala | Asp | Ala | Leu | Ser | Ser | Glu | Gly | Gly | Arg | |
| | | 275 | | | | | 280 | | | | | 285 | | | | |
| CCG | CTG | ACC | CTC | ATC | GCC | GAG | TCC | GAC | CTC | AAC | AAT | CCG | CGG | CTG | CTG | 912 |
| Pro | Leu | Thr | Leu | Ile | Ala | Glu | Ser | Asp | Leu | Asn | Asn | Pro | Arg | Leu | Leu | |
| | | 290 | | | | | 295 | | | | | 300 | | | | |
| TAC | CCC | CGG | GAT | GTC | AAC | GGC | TAC | GGA | CTG | GCC | GGC | CAG | TGG | AGC | GAC | 960 |
| Tyr | Pro | Arg | Asp | Val | Asn | Gly | Tyr | Gly | Leu | Ala | Gly | Gln | Trp | Ser | Asp | |
| 305 | | | | | 310 | | | | | 315 | | | | | 320 | |
| GAC | TTC | CAC | CAC | GCC | GTG | CAC | GTC | AAC | GTC | AGC | GGG | GAA | ACC | ACC | GGC | 1008 |
| Asp | Phe | His | His | Ala | Val | His | Val | Asn | Val | Ser | Gly | Glu | Thr | Thr | Gly | |
| | | | | 325 | | | | | 330 | | | | | 335 | | |
| TAC | TAC | AGC | GAC | TTC | GAC | TCG | CTC | GGA | GCC | CTC | GCC | AAG | GTC | CTG | CGT | 1056 |

|     |     |     |     |     |     |     |     |     |     |     |     |     |     |     |     |
| --- | --- | --- | --- | --- | --- | --- | --- | --- | --- | --- | --- | --- | --- | --- | --- |
| Tyr | Tyr | Ser | Asp<br>340 | Phe | Asp | Ser | Leu | Gly<br>345 | Ala | Leu | Ala | Lys | Val<br>350 | Leu | Arg |

| GAC | GGG | TTC | TTC | CAC | GAC | GGC | AGC | TAC | TCC | AGC | TTC | CGC | GGC | CGC | TGC | 1104 |
| --- | --- | --- | --- | --- | --- | --- | --- | --- | --- | --- | --- | --- | --- | --- | --- | --- |
| Asp | Gly | Phe<br>355 | Phe | His | Asp | Gly | Ser<br>360 | Tyr | Ser | Ser | Phe | Arg<br>365 | Gly | Arg | Cys |  |
| CAC | GGC | CGG | CCG | ATC | AAC | TTC | AGC | GCC | GTG | CAT | CCG | GCC | GCG | CTG | GTG | 1152 |
| His | Gly<br>370 | Arg | Pro | Ile | Asn | Phe<br>375 | Ser | Ala | Val | His | Pro<br>380 | Ala | Ala | Leu | Val |  |
| GTC | TGC | TCA | CAG | AAC | CAT | GAC | CAG | ATC | GGC | AAC | CGG | GCC | ACC | GGG | GAC | 1200 |
| Val<br>385 | Cys | Ser | Gln | Asn | His<br>390 | Asp | Gln | Ile | Gly | Asn<br>395 | Arg | Ala | Thr | Gly | Asp<br>400 |  |
| CGG | CTG | TCC | CAG | TCA | CTT | CCG | TAC | GGC | AGC | CTG | GCC | CTG | GCC | GCC | GTG | 1248 |
| Arg | Leu | Ser | Gln | Ser<br>405 | Leu | Pro | Tyr | Gly | Ser<br>410 | Leu | Ala | Leu | Ala | Ala<br>415 | Val |  |
| CTG | ACC | CTC | ACC | GGT | CCG | TTC | ACG | CCC | ATG | CTG | TTC | ATG | GGA | GAG | GAA | 1296 |
| Leu | Thr | Leu | Thr<br>420 | Gly | Pro | Phe | Thr | Pro<br>425 | Met | Leu | Phe | Met | Gly<br>430 | Glu | Glu |  |
| TAC | GGG | GCC | ACC | ACC | CCG | TGG | CAG | TTC | TTC | ACC | TCG | CAC | CCT | GAA | CCC | 1344 |
| Tyr | Gly | Ala<br>435 | Thr | Thr | Pro | Trp | Gln<br>440 | Phe | Phe | Thr | Ser | His<br>445 | Pro | Glu | Pro |  |
| GAG | CTG | GGC | AAG | GCC | ACG | GCC | GAG | GGC | AGG | ATC | AGG | GAG | TTC | GAG | CGC | 1392 |
| Glu | Leu<br>450 | Gly | Lys | Ala | Thr | Ala<br>455 | Glu | Gly | Arg | Ile | Arg<br>460 | Glu | Phe | Glu | Arg |  |
| ATG | GGG | TGG | GAT | CCC | GCC | GTC | GTG | CCC | GAT | CCG | CAG | GAT | CCG | GAG | ACC | 1440 |
| Met<br>465 | Gly | Trp | Asp | Pro | Ala<br>470 | Val | Val | Pro | Asp | Pro<br>475 | Gln | Asp | Pro | Glu | Thr<br>480 |  |
| TTC | ACC | CGC | TCC | AAA | CTG | GAC | TGG | GCG | GAA | GCG | TCC | GCC | GGC | GAT | CAT | 1488 |
| Phe | Thr | Arg | Ser | Lys<br>485 | Leu | Asp | Trp | Ala | Glu<br>490 | Ala | Ser | Ala | Gly | Asp<br>495 | His |  |
| GCC | CGC | CTC | CTG | GAG | CTG | TAC | CGC | TCG | CTT | ATC | ACG | CTG | CGG | CGG | TCA | 1536 |
| Ala | Arg | Leu | Leu<br>500 | Glu | Leu | Tyr | Arg | Ser<br>505 | Leu | Ile | Thr | Leu | Arg<br>510 | Arg | Ser |  |
| ACT | CCG | GAG | CTC | GCG | CGC | CTG | GGC | TTT | GCG | GAC | ACC | GCC | GTC | GAG | TTC | 1584 |
| Thr | Pro | Glu | Leu<br>515 | Ala | Arg | Leu | Gly | Phe<br>520 | Ala | Asp | Thr | Ala | Val<br>525 | Glu | Phe |  |
| GAC | GAC | GAC | GCC | CGC | TGG | CTC | CGT | TAT | TGG | CGC | GGA | GGC | GTG | CAG | GTG | 1632 |
| Asp | Asp | Asp<br>530 | Ala | Arg | Trp | Leu | Arg<br>535 | Tyr | Trp | Arg | Gly | Gly<br>540 | Val | Gln | Val |  |
| GTG | CTG | AAC | TTC | GCG | GAC | CGT | CCC | ATC | AGC | CTG | GAC | CGG | CCG | GGA | ACC | 1680 |
| Val<br>545 | Leu | Asn | Phe | Ala | Asp<br>550 | Arg | Pro | Ile | Ser | Leu<br>555 | Asp | Arg | Pro | Gly | Thr<br>560 |  |
| GCG | CTG | CTG | CTC | GCC | ACC | GAC | GAC | GCC | GTC | CGG | ATG | GAC | GGA | GTC | CAG | 1728 |
| Ala | Leu | Leu | Leu | Ala<br>565 | Thr | Asp | Asp | Ala | Val<br>570 | Arg | Met | Asp | Gly | Val<br>575 | Gln |  |
| GTG | GAG | CTG | CCG | CCG | CTG | AGC | GCC | GCG | GTT | CTG | CGC | GAC |  |  |  | 1767 |
| Val | Glu | Leu | Pro<br>580 | Pro | Leu | Ser | Ala | Ala<br>585 | Val | Leu | Arg | Asp |  |  |  |  |

( 2 ) INFORMATION FOR SEQ ID NO:2:

( i ) SEQUENCE CHARACTERISTICS:
        ( A ) LENGTH: 589 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Ala | Lys | Pro | Val | Gln | Gly | Ala | Gly | Arg | Phe | Asp | Ile | Trp | Ala | Pro | Glu |
| --- | --- | --- | --- | --- | --- | --- | --- | --- | --- | --- | --- | --- | --- | --- | --- |
| 1 |  |  |  | 5 |  |  |  |  | 10 |  |  |  |  | 15 |  |
| Ala | Gly | Thr | Val | Thr | Leu | Leu | Ala | Gly | Gly | Glu | Arg | Tyr | Glu | Met | Gly |
|  |  |  | 20 |  |  |  |  | 25 |  |  |  |  | 30 |  |  |

```
Arg  Arg  Pro  Gly  Asn  Gly  Pro  Ala  Asp  Glu  Gly  Trp  Trp  Thr  Ala  Ala
          35                       40                      45

Asp  Ala  Pro  Thr  Gly  Ala  Asp  Val  Asp  Tyr  Gly  Tyr  Leu  Leu  Asp  Gly
     50                  55                      60

Asp  Glu  Ile  Pro  Leu  Pro  Asp  Pro  Arg  Thr  Arg  Arg  Gln  Pro  Glu  Gly
65                       70                 75                                80

Val  His  Ala  Leu  Ser  Arg  Thr  Phe  Asp  Pro  Gly  Ala  His  Arg  Trp  Gln
                    85                      90                            95

Asp  Ala  Gly  Trp  Gln  Gly  Arg  Glu  Leu  Gln  Gly  Ser  Val  Ile  Tyr  Glu
               100                      105                      110

Leu  His  Ile  Gly  Thr  Phe  Thr  Pro  Glu  Gly  Thr  Leu  Asp  Ala  Ala  Ala
          115                      120                      125

Gly  Lys  Leu  Asp  Tyr  Leu  Ala  Gly  Leu  Gly  Ile  Asp  Phe  Ile  Glu  Leu
     130                      135                      140

Leu  Pro  Val  Asn  Ala  Phe  Asn  Gly  Thr  His  Asn  Trp  Gly  Tyr  Asp  Gly
145                      150                      155                      160

Val  Gln  Trp  Phe  Ala  Val  His  Glu  Gly  Tyr  Gly  Gly  Pro  Ala  Ala  Tyr
               165                      170                      175

Gln  Arg  Phe  Val  Asp  Ala  Ala  His  Ala  Ala  Gly  Leu  Gly  Val  Ile  Gln
               180                      185                      190

Asp  Val  Val  Tyr  Asn  His  Leu  Gly  Pro  Ser  Gly  Asn  Tyr  Leu  Pro  Arg
          195                      200                      205

Tyr  Gly  Pro  Tyr  Leu  Lys  His  Gly  Glu  Gly  Asn  Thr  Trp  Gly  Asp  Ser
     210                      215                      220

Val  Asn  Leu  Asp  Gly  Pro  Gly  Ser  Asp  His  Val  Arg  Gln  Tyr  Ile  Leu
225                      230                      235                      240

Asp  Asn  Val  Ala  Met  Trp  Leu  Arg  Asp  Tyr  Arg  Val  Asp  Gly  Leu  Arg
               245                      250                      255

Leu  Asp  Ala  Val  His  Ala  Leu  Lys  Asp  Glu  Arg  Ala  Val  His  Ile  Leu
               260                      265                      270

Glu  Glu  Phe  Gly  Ala  Leu  Ala  Asp  Ala  Leu  Ser  Ser  Glu  Gly  Gly  Arg
          275                      280                      285

Pro  Leu  Thr  Leu  Ile  Ala  Glu  Ser  Asp  Leu  Asn  Asn  Pro  Arg  Leu  Leu
     290                      295                      300

Tyr  Pro  Arg  Asp  Val  Asn  Gly  Tyr  Gly  Leu  Ala  Gly  Gln  Trp  Ser  Asp
305                      310                      315                      320

Asp  Phe  His  His  Ala  Val  His  Val  Asn  Val  Ser  Gly  Glu  Thr  Thr  Gly
               325                      330                      335

Tyr  Tyr  Ser  Asp  Phe  Asp  Ser  Leu  Gly  Ala  Leu  Ala  Lys  Val  Leu  Arg
          340                      345                      350

Asp  Gly  Phe  Phe  His  Asp  Gly  Ser  Tyr  Ser  Ser  Phe  Arg  Gly  Arg  Cys
          355                      360                      365

His  Gly  Arg  Pro  Ile  Asn  Phe  Ser  Ala  Val  His  Pro  Ala  Ala  Leu  Val
     370                      375                      380

Val  Cys  Ser  Gln  Asn  His  Asp  Gln  Ile  Gly  Asn  Arg  Ala  Thr  Gly  Asp
385                      390                      395                      400

Arg  Leu  Ser  Gln  Ser  Leu  Pro  Tyr  Gly  Ser  Leu  Ala  Leu  Ala  Ala  Val
                    405                      410                      415

Leu  Thr  Leu  Thr  Gly  Pro  Phe  Thr  Pro  Met  Leu  Phe  Met  Gly  Glu  Glu
               420                      425                      430

Tyr  Gly  Ala  Thr  Thr  Pro  Trp  Gln  Phe  Phe  Thr  Ser  His  Pro  Glu  Pro
          435                      440                      445

Glu  Leu  Gly  Lys  Ala  Thr  Ala  Glu  Gly  Arg  Ile  Arg  Glu  Phe  Glu  Arg
```

|     | 450 |     |     |     |     | 455 |     |     |     |     | 460 |     |     |     |
|-----|-----|-----|-----|-----|-----|-----|-----|-----|-----|-----|-----|-----|-----|-----|
| Met | Gly | Trp | Asp | Pro | Ala | Val | Val | Pro | Asp | Pro | Gln | Asp | Pro | Glu | Thr |
| 465 |     |     |     |     | 470 |     |     |     | 475 |     |     |     |     | 480 |

Phe Thr Arg Ser Lys Leu Asp Trp Ala Glu Ala Ser Ala Gly Asp His
                485                 490                 495

Ala Arg Leu Leu Glu Leu Tyr Arg Ser Leu Ile Thr Leu Arg Arg Ser
            500                 505                 510

Thr Pro Glu Leu Ala Arg Leu Gly Phe Ala Asp Thr Ala Val Glu Phe
        515                 520                 525

Asp Asp Asp Ala Arg Trp Leu Arg Tyr Trp Arg Gly Gly Val Gln Val
    530                 535                 540

Val Leu Asn Phe Ala Asp Arg Pro Ile Ser Leu Asp Arg Pro Gly Thr
545                 550                 555                 560

Ala Leu Leu Leu Ala Thr Asp Asp Ala Val Arg Met Asp Gly Val Gln
                565                 570                 575

Val Glu Leu Pro Pro Leu Ser Ala Ala Val Leu Arg Asp
            580                 585

( 2 ) INFORMATION FOR SEQ ID NO:3:

( i ) SEQUENCE CHARACTERISTICS:
        ( A ) LENGTH: 1791 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..1791

( x i ) SEQUENCE DESCRIPTION: SEQ ID NO:3:

```
ACG  CAC  ACC  TAC  CCG  CGG  GAA  GCC  GCG  AAA  CCC  GTC  CTG  GGC  CCC  GCA         48
Thr  His  Thr  Tyr  Pro  Arg  Glu  Ala  Ala  Lys  Pro  Val  Leu  Gly  Pro  Ala
590                      595                      600                      605

CGC  TAC  GAC  GTC  TGG  GCG  CCC  AAC  GCT  GAA  TCC  GTG  ACG  CTG  CTG  GCC         96
Arg  Tyr  Asp  Val  Trp  Ala  Pro  Asn  Ala  Glu  Ser  Val  Thr  Leu  Leu  Ala
                     610                      615                      620

GGC  GGG  GAG  CGC  TAC  GCC  ATG  CAG  CGC  CGG  GCC  GAG  ACC  GGG  CCG  GAG        144
Gly  Gly  Glu  Arg  Tyr  Ala  Met  Gln  Arg  Arg  Ala  Glu  Thr  Gly  Pro  Glu
               625                      630                      635

GAC  GCC  GGC  TGG  TGG  ACC  GCC  GCC  GGC  GCG  CCT  ACG  GAT  GGC  AAC  GTG        192
Asp  Ala  Gly  Trp  Trp  Thr  Ala  Ala  Gly  Ala  Pro  Thr  Asp  Gly  Asn  Val
          640                      645                      650

GAC  TAC  GGG  TAC  CTT  CTG  GAC  GGC  GAC  GAA  ACA  CCG  CTT  CCG  GAT  CCA        240
Asp  Tyr  Gly  Tyr  Leu  Leu  Asp  Gly  Asp  Glu  Thr  Pro  Leu  Pro  Asp  Pro
     655                      660                      665

CGG  ACC  CGC  CGC  CAG  CCC  GAC  GGC  GTC  CAC  GCC  CTG  TCC  CGC  ACG  TTC        288
Arg  Thr  Arg  Arg  Gln  Pro  Asp  Gly  Val  His  Ala  Leu  Ser  Arg  Thr  Phe
670                      675                      680                      685

GAC  CCG  TCC  GCG  TAC  AGC  TGG  CAG  GAC  GAC  GCC  TGG  CAG  GGC  AGG  GAA        336
Asp  Pro  Ser  Ala  Tyr  Ser  Trp  Gln  Asp  Asp  Ala  Trp  Gln  Gly  Arg  Glu
                    690                      695                      700

CTG  CAG  GGC  GCC  GTC  ATC  TAC  GAG  CTC  CAC  CTC  GGA  ACA  TTC  ACG  CCC        384
Leu  Gln  Gly  Ala  Val  Ile  Tyr  Glu  Leu  His  Leu  Gly  Thr  Phe  Thr  Pro
               705                      710                      715

GAA  GGG  ACG  CTG  GAG  GCG  GCC  GCC  GGA  AAG  CTG  GAC  TAC  CTC  GCC  GGC        432
Glu  Gly  Thr  Leu  Glu  Ala  Ala  Ala  Gly  Lys  Leu  Asp  Tyr  Leu  Ala  Gly
          720                      725                      730

TTG  GGC  GTC  GAC  TTC  ATC  GAG  CTG  CTG  CCG  GTG  AAC  GCT  TTC  AAC  GGC        480
```

|   |   |   |   |   |   |   |   |   |   |   |   |   |   |   |   |
|---|---|---|---|---|---|---|---|---|---|---|---|---|---|---|---|
| Leu | Gly | Val | Asp | Phe | Ile | Glu | Leu | Leu | Pro | Val | Asn | Ala | Phe | Asn | Gly |
|  | 735 |  |  |  | 740 |  |  |  |  | 745 |  |  |  |  |  |

| ACG | CAC | AAC | TGG | GGT | TAC | GAC | GGT | GTC | CAG | TGG | TTC | GCT | GTG | CAC | GAG | 528 |
|---|---|---|---|---|---|---|---|---|---|---|---|---|---|---|---|---|
| Thr | His | Asn | Trp | Gly | Tyr | Asp | Gly | Val | Gln | Trp | Phe | Ala | Val | His | Glu |  |
| 750 |  |  |  |  | 755 |  |  |  |  | 760 |  |  |  |  | 765 |  |

| GCA | TAC | GGC | GGG | CCG | GAA | GCG | TAC | CAG | CGG | TTC | GTC | GAC | GCC | GCC | CAC | 576 |
|---|---|---|---|---|---|---|---|---|---|---|---|---|---|---|---|---|
| Ala | Tyr | Gly | Gly | Pro | Glu | Ala | Tyr | Gln | Arg | Phe | Val | Asp | Ala | Ala | His |  |
|  |  |  |  | 770 |  |  |  |  | 775 |  |  |  |  |  | 780 |  |

| GCC | GCA | GGC | CTT | GGC | GTG | ATC | CAG | GAC | GTG | GTC | TAC | AAC | CAC | CTC | GGC | 624 |
|---|---|---|---|---|---|---|---|---|---|---|---|---|---|---|---|---|
| Ala | Ala | Gly | Leu | Gly | Val | Ile | Gln | Asp | Val | Val | Tyr | Asn | His | Leu | Gly |  |
|  |  |  |  | 785 |  |  |  |  | 790 |  |  |  |  | 795 |  |  |

| CCC | AGC | GGG | AAC | TAC | CTG | CCG | CGG | TTC | GGG | CCG | TAC | CTC | AAG | CAG | GGC | 672 |
|---|---|---|---|---|---|---|---|---|---|---|---|---|---|---|---|---|
| Pro | Ser | Gly | Asn | Tyr | Leu | Pro | Arg | Phe | Gly | Pro | Tyr | Leu | Lys | Gln | Gly |  |
|  |  | 800 |  |  |  |  | 805 |  |  |  |  | 810 |  |  |  |  |

| GAG | GGT | AAC | ACG | TGG | GGC | GAC | TCG | GTG | AAC | CTG | GAC | GGG | CCC | GGC | TCC | 720 |
|---|---|---|---|---|---|---|---|---|---|---|---|---|---|---|---|---|
| Glu | Gly | Asn | Thr | Trp | Gly | Asp | Ser | Val | Asn | Leu | Asp | Gly | Pro | Gly | Ser |  |
|  | 815 |  |  |  |  | 820 |  |  |  |  | 825 |  |  |  |  |  |

| GAC | CAT | GTG | CGC | CGG | TAC | ATC | CTG | GAC | AAC | CTG | GCC | ATG | TGG | CTG | CGT | 768 |
|---|---|---|---|---|---|---|---|---|---|---|---|---|---|---|---|---|
| Asp | His | Val | Arg | Arg | Tyr | Ile | Leu | Asp | Asn | Leu | Ala | Met | Trp | Leu | Arg |  |
| 830 |  |  |  |  | 835 |  |  |  |  | 840 |  |  |  |  | 845 |  |

| GAC | TAC | CGG | GTG | GAC | GGC | CTG | CGG | CTG | GAC | GCC | GTC | CAC | GCC | CTG | AAG | 816 |
|---|---|---|---|---|---|---|---|---|---|---|---|---|---|---|---|---|
| Asp | Tyr | Arg | Val | Asp | Gly | Leu | Arg | Leu | Asp | Ala | Val | His | Ala | Leu | Lys |  |
|  |  |  |  | 850 |  |  |  |  | 855 |  |  |  |  | 860 |  |  |

| GAT | GAG | CGG | GCG | GTG | CAC | ATC | CTG | GAG | GAC | TTC | GGG | GCG | CTG | GCC | GAT | 864 |
|---|---|---|---|---|---|---|---|---|---|---|---|---|---|---|---|---|
| Asp | Glu | Arg | Ala | Val | His | Ile | Leu | Glu | Asp | Phe | Gly | Ala | Leu | Ala | Asp |  |
|  |  |  |  | 865 |  |  |  |  | 870 |  |  |  |  | 875 |  |  |

| CAG | ATC | TCC | GCC | GAG | GTG | GGA | CGG | CCG | CTG | ACG | CTC | ATC | GCC | GAG | TCC | 912 |
|---|---|---|---|---|---|---|---|---|---|---|---|---|---|---|---|---|
| Gln | Ile | Ser | Ala | Glu | Val | Gly | Arg | Pro | Leu | Thr | Leu | Ile | Ala | Glu | Ser |  |
|  |  | 880 |  |  |  |  | 885 |  |  |  |  | 890 |  |  |  |  |

| GAC | CTC | AAC | AAC | CCG | CGG | CTG | CTG | TAC | CCG | CGG | GAC | GTC | AAC | GGG | TAC | 960 |
|---|---|---|---|---|---|---|---|---|---|---|---|---|---|---|---|---|
| Asp | Leu | Asn | Asn | Pro | Arg | Leu | Leu | Tyr | Pro | Arg | Asp | Val | Asn | Gly | Tyr |  |
| 895 |  |  |  |  | 900 |  |  |  |  | 905 |  |  |  |  |  |  |

| GGG | CTG | GAA | GGG | CAG | TGG | AGC | GAC | GAC | TTC | CAC | CAC | GCC | GTC | CAC | GTC | 1008 |
|---|---|---|---|---|---|---|---|---|---|---|---|---|---|---|---|---|
| Gly | Leu | Glu | Gly | Gln | Trp | Ser | Asp | Asp | Phe | His | His | Ala | Val | His | Val |  |
| 910 |  |  |  |  | 915 |  |  |  |  | 920 |  |  |  |  | 925 |  |

| AAC | GTC | ACC | GGC | GAA | ACC | ACC | GGC | TAC | TAC | AGT | GAC | TTC | GAC | TCG | CTG | 1056 |
|---|---|---|---|---|---|---|---|---|---|---|---|---|---|---|---|---|
| Asn | Val | Thr | Gly | Glu | Thr | Thr | Gly | Tyr | Tyr | Ser | Asp | Phe | Asp | Ser | Leu |  |
|  |  |  | 930 |  |  |  |  | 935 |  |  |  |  | 940 |  |  |  |

| GCC | GCC | CTC | GCC | AAG | GTG | CTC | CGG | GAC | GGC | TTC | TTC | CAC | GAC | GGC | AGC | 1104 |
|---|---|---|---|---|---|---|---|---|---|---|---|---|---|---|---|---|
| Ala | Ala | Leu | Ala | Lys | Val | Leu | Arg | Asp | Gly | Phe | Phe | His | Asp | Gly | Ser |  |
|  |  |  | 945 |  |  |  |  | 950 |  |  |  |  | 955 |  |  |  |

| TAC | TCC | AGC | TTC | CGG | GAA | CGC | CAC | CAC | GGA | CGG | CCG | ATT | AAT | TTC | AGC | 1152 |
|---|---|---|---|---|---|---|---|---|---|---|---|---|---|---|---|---|
| Tyr | Ser | Ser | Phe | Arg | Glu | Arg | His | His | Gly | Arg | Pro | Ile | Asn | Phe | Ser |  |
|  |  | 960 |  |  |  |  | 965 |  |  |  |  | 970 |  |  |  |  |

| GCC | GTA | CAC | CCA | GCC | GCC | CTG | GTG | GTC | TGT | TCG | CAG | AAC | CAC | GAC | CAG | 1200 |
|---|---|---|---|---|---|---|---|---|---|---|---|---|---|---|---|---|
| Ala | Val | His | Pro | Ala | Ala | Leu | Val | Val | Cys | Ser | Gln | Asn | His | Asp | Gln |  |
|  | 975 |  |  |  |  | 980 |  |  |  |  | 985 |  |  |  |  |  |

| ATC | GGC | AAC | CGT | GCC | ACG | GGG | GAC | CGG | CTC | TCC | CAG | ACC | CTG | CCG | TAC | 1248 |
|---|---|---|---|---|---|---|---|---|---|---|---|---|---|---|---|---|
| Ile | Gly | Asn | Arg | Ala | Thr | Gly | Asp | Arg | Leu | Ser | Gln | Thr | Leu | Pro | Tyr |  |
| 990 |  |  |  |  | 995 |  |  |  |  | 1000 |  |  |  |  | 1005 |  |

| GGA | AGC | CTG | GCC | CTC | GCT | GCG | GTG | CTG | ACC | CTG | ACG | GGA | CCC | TTC | ACG | 1296 |
|---|---|---|---|---|---|---|---|---|---|---|---|---|---|---|---|---|
| Gly | Ser | Leu | Ala | Leu | Ala | Ala | Val | Leu | Thr | Leu | Thr | Gly | Pro | Phe | Thr |  |
|  |  |  |  | 1010 |  |  |  |  | 1015 |  |  |  |  | 1020 |  |  |

| CCC | ATG | CTG | CTC | ATG | GGC | GAG | GAG | TAC | GGC | GCC | AGC | ACG | CCG | TGG | CAG | 1344 |
|---|---|---|---|---|---|---|---|---|---|---|---|---|---|---|---|---|
| Pro | Met | Leu | Leu | Met | Gly | Glu | Glu | Tyr | Gly | Ala | Ser | Thr | Pro | Trp | Gln |  |
|  |  |  |  | 1025 |  |  |  |  | 1030 |  |  |  |  | 1035 |  |  |

| TTT | TTC | ACC | TCG | CAC | CCG | GAG | CCG | GAG | CTC | GGC | AAG | GCC | ACC | GCG | GAG | 1392 |
|---|---|---|---|---|---|---|---|---|---|---|---|---|---|---|---|---|
| Phe | Phe | Thr | Ser | His | Pro | Glu | Pro | Glu | Leu | Gly | Lys | Ala | Thr | Ala | Glu |  |
|  |  |  | 1040 |  |  |  |  | 1045 |  |  |  |  | 1050 |  |  |  |

| GGC | CGG | ATC | AAG | GAG | TTC | GAG | CGC | ATG | GGG | TGG | GAT | CCC | GCC | GTC | GTG | 1440 |
|---|---|---|---|---|---|---|---|---|---|---|---|---|---|---|---|---|

-continued

| | | | | | | | | | | | | | | | |
|---|---|---|---|---|---|---|---|---|---|---|---|---|---|---|---|
|Gly|Arg|Ile|Lys|Glu|Phe|Glu|Arg|Met|Gly|Trp|Asp|Pro|Ala|Val|Val|
| | |1055| | |1060| | | |1065| | | | | | |

```
CCC GAT CCC CAG GAT CCT GAG ACG TTC CGC CGG TCC AAG CTG GAC TGG    1488
Pro Asp Pro Gln Asp Pro Glu Thr Phe Arg Arg Ser Lys Leu Asp Trp
1070            1075                1080                1085

GCG GAA GCC GCC GAA GGC GAC CAT GCC CGG CTG CTG GAG CTG TAC CGT    1536
Ala Glu Ala Ala Glu Gly Asp His Ala Arg Leu Leu Glu Leu Tyr Arg
        1090                1095                1100

TCG CTC ACC GCC CTG CGC CGC TCC ACG CCG GAC CTC ACC AAG CTG GGC    1584
Ser Leu Thr Ala Leu Arg Arg Ser Thr Pro Asp Leu Thr Lys Leu Gly
            1105                1110                1115

TTC GAG GAC ACG CAG GTG GCG TTC GAC GAG GAC GCC CGC TGG CTG CGG    1632
Phe Glu Asp Thr Gln Val Ala Phe Asp Glu Asp Ala Arg Trp Leu Arg
        1120                1125                1130

TTC CGC CGG GGT GGC GTG CAG GTG CTG CTC AAC TTC TCG GAA CAG CCC    1680
Phe Arg Arg Gly Gly Val Gln Val Leu Leu Asn Phe Ser Glu Gln Pro
    1135                1140                1145

GTG AGC CTG GAC GGG GCG GGC ACG GCC CTG CTG CTG GCC ACC GAC GAC    1728
Val Ser Leu Asp Gly Ala Gly Thr Ala Leu Leu Leu Ala Thr Asp Asp
1150                1155                1160                1165

GCC GTC CGG CTA GAA GGT GAG CGT GCG GAA CTC GGT CCG CTG AGC GCC    1776
Ala Val Arg Leu Glu Gly Glu Arg Ala Glu Leu Gly Pro Leu Ser Ala
        1170                1175                1180

GCC GTC GTC AGC GAC                                                1791
Ala Val Val Ser Asp
    1185
```

( 2 ) INFORMATION FOR SEQ ID NO:4:

( i ) SEQUENCE CHARACTERISTICS:
        ( A ) LENGTH: 597 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Thr His Thr Tyr Pro Arg Glu Ala Ala Lys Pro Val Leu Gly Pro Ala
 1               5                  10                  15

Arg Tyr Asp Val Trp Ala Pro Asn Ala Glu Ser Val Thr Leu Leu Ala
            20                  25                  30

Gly Gly Glu Arg Tyr Ala Met Gln Arg Arg Ala Glu Thr Gly Pro Glu
        35                  40                  45

Asp Ala Gly Trp Trp Thr Ala Ala Gly Ala Pro Thr Asp Gly Asn Val
    50                  55                  60

Asp Tyr Gly Tyr Leu Leu Asp Gly Asp Glu Thr Pro Leu Pro Asp Pro
65                  70                  75                  80

Arg Thr Arg Arg Gln Pro Asp Gly Val His Ala Leu Ser Arg Thr Phe
            85                  90                  95

Asp Pro Ser Ala Tyr Ser Trp Gln Asp Asp Ala Trp Gln Gly Arg Glu
        100                 105                 110

Leu Gln Gly Ala Val Ile Tyr Glu Leu His Leu Gly Thr Phe Thr Pro
    115                 120                 125

Glu Gly Thr Leu Glu Ala Ala Ala Gly Lys Leu Asp Tyr Leu Ala Gly
130                 135                 140

Leu Gly Val Asp Phe Ile Glu Leu Leu Pro Val Asn Ala Phe Asn Gly
145                 150                 155                 160

Thr His Asn Trp Gly Tyr Asp Gly Val Gln Trp Phe Ala Val His Glu
            165                 170                 175
```

-continued

| | | | | | | | | | | | | | | |
|---|---|---|---|---|---|---|---|---|---|---|---|---|---|---|
| Ala | Tyr | Gly | Gly<br>180 | Pro | Glu | Ala | Tyr<br>185 | Gln | Arg | Phe | Val | Asp<br>190 | Ala | His |
| Ala | Ala | Gly<br>195 | Leu | Gly | Val | Ile<br>200 | Gln | Asp | Val | Val | Tyr<br>205 | Asn | His | Leu | Gly |
| Pro | Ser<br>210 | Gly | Asn | Tyr | Leu | Pro<br>215 | Arg | Phe | Gly | Pro | Tyr<br>220 | Leu | Lys | Gln | Gly |
| Glu<br>225 | Gly | Asn | Thr | Trp | Gly<br>230 | Asp | Ser | Val | Asn | Leu<br>235 | Asp | Gly | Pro | Gly | Ser<br>240 |
| Asp | His | Val | Arg | Arg<br>245 | Tyr | Ile | Leu | Asp | Asn<br>250 | Leu | Ala | Met | Trp | Leu<br>255 | Arg |
| Asp | Tyr | Arg | Val<br>260 | Asp | Gly | Leu | Arg | Leu<br>265 | Asp | Ala | Val | His | Ala<br>270 | Leu | Lys |
| Asp | Glu | Arg<br>275 | Ala | Val | His | Ile | Leu<br>280 | Glu | Asp | Phe | Gly | Ala<br>285 | Leu | Ala | Asp |
| Gln | Ile<br>290 | Ser | Ala | Glu | Val | Gly<br>295 | Arg | Pro | Leu | Thr | Leu<br>300 | Ile | Ala | Glu | Ser |
| Asp<br>305 | Leu | Asn | Asn | Pro | Arg<br>310 | Leu | Leu | Tyr | Pro | Arg<br>315 | Asp | Val | Asn | Gly | Tyr<br>320 |
| Gly | Leu | Glu | Gly | Gln<br>325 | Trp | Ser | Asp | Asp | Phe<br>330 | His | His | Ala | Val | His<br>335 | Val |
| Asn | Val | Thr | Gly<br>340 | Glu | Thr | Thr | Gly | Tyr<br>345 | Tyr | Ser | Asp | Phe | Asp<br>350 | Ser | Leu |
| Ala | Ala | Leu | Ala<br>355 | Lys | Val | Leu | Arg<br>360 | Asp | Gly | Phe | Phe | His<br>365 | Asp | Gly | Ser |
| Tyr | Ser<br>370 | Ser | Phe | Arg | Glu | Arg<br>375 | His | His | Gly | Arg | Pro<br>380 | Ile | Asn | Phe | Ser |
| Ala<br>385 | Val | His | Pro | Ala | Ala<br>390 | Leu | Val | Val | Cys | Ser<br>395 | Gln | Asn | His | Asp | Gln<br>400 |
| Ile | Gly | Asn | Arg | Ala<br>405 | Thr | Gly | Asp | Arg | Leu<br>410 | Ser | Gln | Thr | Leu | Pro<br>415 | Tyr |
| Gly | Ser | Leu | Ala<br>420 | Leu | Ala | Ala | Val | Leu<br>425 | Thr | Leu | Thr | Gly | Pro<br>430 | Phe | Thr |
| Pro | Met | Leu<br>435 | Leu | Met | Gly | Glu<br>440 | Glu | Tyr | Gly | Ala | Ser<br>445 | Thr | Pro | Trp | Gln |
| Phe | Phe<br>450 | Thr | Ser | His | Pro<br>455 | Glu | Pro | Glu | Leu | Gly<br>460 | Lys | Ala | Thr | Ala | Glu |
| Gly<br>465 | Arg | Ile | Lys | Glu | Phe<br>470 | Glu | Arg | Met | Gly | Trp<br>475 | Asp | Pro | Ala | Val | Val<br>480 |
| Pro | Asp | Pro | Gln | Asp<br>485 | Pro | Glu | Thr | Phe | Arg<br>490 | Arg | Ser | Lys | Leu | Asp<br>495 | Trp |
| Ala | Glu | Ala | Ala<br>500 | Glu | Gly | Asp | His | Ala<br>505 | Arg | Leu | Leu | Glu | Leu<br>510 | Tyr | Arg |
| Ser | Leu | Thr<br>515 | Ala | Leu | Arg | Arg | Ser<br>520 | Thr | Pro | Asp | Leu | Thr<br>525 | Lys | Leu | Gly |
| Phe | Glu<br>530 | Asp | Thr | Gln | Val | Ala<br>535 | Phe | Asp | Glu | Asp | Ala<br>540 | Arg | Trp | Leu | Arg |
| Phe<br>545 | Arg | Arg | Gly | Gly | Val<br>550 | Gln | Val | Leu | Leu | Asn<br>555 | Phe | Ser | Glu | Gln | Pro<br>560 |
| Val | Ser | Leu | Asp | Gly<br>565 | Ala | Gly | Thr | Ala | Leu<br>570 | Leu | Leu | Ala | Thr | Asp<br>575 | Asp |
| Ala | Val | Arg | Leu<br>580 | Glu | Gly | Glu | Arg | Ala<br>585 | Glu | Leu | Gly | Pro<br>590 | Leu | Ser | Ala |
| Ala | Val | Val | Ser<br>595 | Asp | | | | | | | | | | | |

( 2 ) INFORMATION FOR SEQ ID NO:5:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
Ala Lys Pro Val Gln Gly Ala Gly Arg Phe Asp Ile Trp Ala Pro Glu
 1               5                  10                  15
Ala Gly Thr Val
             20
```

( 2 ) INFORMATION FOR SEQ ID NO:6:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Thr His Thr Tyr Pro Arg Glu Ala Ala Lys Pro Val Leu Gly Pro Ala
 1               5                  10                  15
Arg Tyr Asp Val
             20
```

( 2 ) INFORMATION FOR SEQ ID NO:7:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
Pro Val Gln Gly Ala Gly Arg Phe Asp Ile Trp Ala Pro Glu Ala Gly
 1               5                  10                  15
Thr Val Thr Leu Leu
             20
```

( 2 ) INFORMATION FOR SEQ ID NO:8:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

```
Leu Asp Trp Ala Glu Ala Ser Ala Gly Asp His Ala Arg Leu Leu Glu
 1               5                  10                  15
Leu
```

( 2 ) INFORMATION FOR SEQ ID NO:9:

( i ) SEQUENCE CHARACTERISTICS:

( A ) LENGTH: 20 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:9:

```
Glu  Phe  Glu  Arg  Met  Gly  Trp  Asp  Pro  Ala  Val  Val  Pro  Asp  Pro  Gln
1                   5                        10                       15

Asp  Pro  Glu  Thr
                20
```

( 2 ) INFORMATION FOR SEQ ID NO:10:

( i ) SEQUENCE CHARACTERISTICS:
( A ) LENGTH: 20 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:10:

```
Pro  Val  Leu  Gly  Pro  Ala  Arg  Tyr  Asp  Val  Trp  Ala  Pro  Asn  Ala  Glu
1                   5                        10                       15

Ser  Val  Thr  Leu
                20
```

( 2 ) INFORMATION FOR SEQ ID NO:11:

( i ) SEQUENCE CHARACTERISTICS:
( A ) LENGTH: 2161 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 207..1994

( x i ) SEQUENCE DESCRIPTION: SEQ ID NO:11:

```
GGCGCCGGGG  GAGTGCTGGC  GCTTGCCACC  CGGCTCCCCT  ACGGGCTGGA  ACAGTCGGGC        60

GGCTGGCGGG  ACACCGCCGT  CGAGCTTGAA  GCCGCCATGA  CGGACGAACT  GACCGGCTCC       120

ACTTTCGGGC  CGGGACCGGC  GGCGCTGTCA  GAAGTCTTCC  GGGCCTACCC  GGTGGCCTTG       180

TTGGTCCCCG  CGACAGGAGG  CAAGTC ATG  ACG  CAG  CCC  AAC  GAT  GCG  GCC  AAG   233
                               Met  Thr  Gln  Pro  Asn  Asp  Ala  Ala  Lys
                                                  600                 605

CCG  GTG  CAG  GGA  GCG  GGG  CGC  TTC  GAT  ATC  TGG  GCG  CCC  GAG  GCA  GGC   281
Pro  Val  Gln  Gly  Ala  Gly  Arg  Phe  Asp  Ile  Trp  Ala  Pro  Glu  Ala  Gly
               610                      615                      620

ACC  GTA  ACG  CTG  CTG  GCC  GGC  GGG  GAG  CGC  TAC  GAG  ATG  GGC  CGC  CGC   329
Thr  Val  Thr  Leu  Leu  Ala  Gly  Gly  Glu  Arg  Tyr  Glu  Met  Gly  Arg  Arg
               625                      630                      635

CCC  GGC  AAC  GGG  CCG  GCG  GAC  GAA  GGC  TGG  TGG  ACG  GCC  GCG  GAT  GCA   377
Pro  Gly  Asn  Gly  Pro  Ala  Asp  Glu  Gly  Trp  Trp  Thr  Ala  Ala  Asp  Ala
               640                      645                      650

CCG  ACA  GGC  GCG  GAC  GTG  GAC  TAC  GGA  TAC  CTG  CTC  GAC  GGC  GAC  GAA   425
Pro  Thr  Gly  Ala  Asp  Val  Asp  Tyr  Gly  Tyr  Leu  Leu  Asp  Gly  Asp  Glu
655                      660                      665                 670

ATC  CCG  CTG  CCG  GAC  CCC  CGG  ACC  CGC  CGC  CAG  CCC  GAA  GGC  GTC  CAT   473
Ile  Pro  Leu  Pro  Asp  Pro  Arg  Thr  Arg  Arg  Gln  Pro  Glu  Gly  Val  His
                         675                      680                 685
```

| | | | | | | | | | | | | | | | | |
|---|---|---|---|---|---|---|---|---|---|---|---|---|---|---|---|---|
| GCC | CTG | TCC | CGG | ACC | TTC | GAC | CCC | GGC | GCC | CAC | CGC | TGG | CAG | GAC | GCC | 521 |
| Ala | Leu | Ser | Arg | Thr | Phe | Asp | Pro | Gly | Ala | His | Arg | Trp | Gln | Asp | Ala | |
| | | | 690 | | | | 695 | | | | | 700 | | | | |
| GGG | TGG | CAG | GGC | AGG | GAA | CTC | CAG | GGC | TCC | GTG | ATT | TAC | GAA | CTC | CAC | 569 |
| Gly | Trp | Gln | Gly | Arg | Glu | Leu | Gln | Gly | Ser | Val | Ile | Tyr | Glu | Leu | His | |
| | | 705 | | | | | 710 | | | | | 715 | | | | |
| ATC | GGA | ACG | TTC | ACG | CCG | GAA | GGG | ACG | CTG | GAC | GCC | GCC | GCG | GGC | AAG | 617 |
| Ile | Gly | Thr | Phe | Thr | Pro | Glu | Gly | Thr | Leu | Asp | Ala | Ala | Ala | Gly | Lys | |
| | 720 | | | | | 725 | | | | | 730 | | | | | |
| CTG | GAC | TAC | CTC | GCC | GGC | CTG | GGC | ATC | GAC | TTC | ATT | GAG | CTG | CTG | CCC | 665 |
| Leu | Asp | Tyr | Leu | Ala | Gly | Leu | Gly | Ile | Asp | Phe | Ile | Glu | Leu | Leu | Pro | |
| 735 | | | | | 740 | | | | | 745 | | | | | 750 | |
| GTG | AAT | GCC | TTC | AAC | GGC | ACG | CAC | AAC | TGG | GGC | TAC | GAC | GGC | GTC | CAG | 713 |
| Val | Asn | Ala | Phe | Asn | Gly | Thr | His | Asn | Trp | Gly | Tyr | Asp | Gly | Val | Gln | |
| | | | | 755 | | | | | 760 | | | | | 765 | | |
| TGG | TTT | GCC | GTG | CAT | GAA | GGC | TAC | GGG | CCT | GCG | GCG | TAC | CAG | CGG | | 761 |
| Trp | Phe | Ala | Val | His | Glu | Gly | Tyr | Gly | Gly | Pro | Ala | Ala | Tyr | Gln | Arg | |
| | | | 770 | | | | | 775 | | | | | 780 | | | |
| TTC | GTG | GAT | GCG | GCC | CAC | GCG | GCC | GGC | CTC | GGC | GTC | ATC | CAG | GAC | GTG | 809 |
| Phe | Val | Asp | Ala | Ala | His | Ala | Ala | Gly | Leu | Gly | Val | Ile | Gln | Asp | Val | |
| | | 785 | | | | | 790 | | | | | 795 | | | | |
| GTC | TAC | AAC | CAC | CTC | GGG | CCG | AGC | GGG | AAC | TAC | CTC | CCC | AGG | TAC | GGC | 857 |
| Val | Tyr | Asn | His | Leu | Gly | Pro | Ser | Gly | Asn | Tyr | Leu | Pro | Arg | Tyr | Gly | |
| | 800 | | | | | 805 | | | | | 810 | | | | | |
| CCG | TAC | CTC | AAG | CAC | GGC | GAA | GGC | AAC | ACC | TGG | GGC | GAT | TCG | GTC | AAC | 905 |
| Pro | Tyr | Leu | Lys | His | Gly | Glu | Gly | Asn | Thr | Trp | Gly | Asp | Ser | Val | Asn | |
| 815 | | | | | 820 | | | | | 825 | | | | | 830 | |
| CTG | GAC | GGG | CCG | GGA | TCC | GAC | CAC | GTC | CGC | CAG | TAC | ATC | CTG | GAC | AAC | 953 |
| Leu | Asp | Gly | Pro | Gly | Ser | Asp | His | Val | Arg | Gln | Tyr | Ile | Leu | Asp | Asn | |
| | | | | 835 | | | | | 840 | | | | | 845 | | |
| GTG | GCC | ATG | TGG | CTG | CGC | GAC | TAC | CGG | GTG | GAC | GGC | CTC | CGC | CTG | GAC | 1001 |
| Val | Ala | Met | Trp | Leu | Arg | Asp | Tyr | Arg | Val | Asp | Gly | Leu | Arg | Leu | Asp | |
| | | | 850 | | | | | 855 | | | | | 860 | | | |
| GCC | GTC | CAC | GCC | CTG | AAG | GAT | GAG | CGG | GCC | GTC | CAC | ATC | CTG | GAG | GAG | 1049 |
| Ala | Val | His | Ala | Leu | Lys | Asp | Glu | Arg | Ala | Val | His | Ile | Leu | Glu | Glu | |
| | | 865 | | | | | 870 | | | | | 875 | | | | |
| TTC | GGC | GCG | CTG | GCG | GAC | GCC | CTG | TCG | TCC | GAA | GGC | GGC | CGC | CCG | CTG | 1097 |
| Phe | Gly | Ala | Leu | Ala | Asp | Ala | Leu | Ser | Ser | Glu | Gly | Gly | Arg | Pro | Leu | |
| | 880 | | | | | 885 | | | | | 890 | | | | | |
| ACC | CTC | ATC | GCC | GAG | TCC | GAC | CTC | AAC | AAT | CCG | CGG | CTG | CTG | TAC | CCC | 1145 |
| Thr | Leu | Ile | Ala | Glu | Ser | Asp | Leu | Asn | Asn | Pro | Arg | Leu | Leu | Tyr | Pro | |
| 895 | | | | | 900 | | | | | 905 | | | | | 910 | |
| CGG | GAT | GTC | AAC | GGC | TAC | GGA | CTG | GCC | GGC | CAG | TGG | AGC | GAC | GAC | TTC | 1193 |
| Arg | Asp | Val | Asn | Gly | Tyr | Gly | Leu | Ala | Gly | Gln | Trp | Ser | Asp | Asp | Phe | |
| | | | | 915 | | | | | 920 | | | | | 925 | | |
| CAC | CAC | GCC | GTG | CAC | GTC | AAC | GTC | AGC | GGG | GAA | ACC | ACC | GGC | TAC | TAC | 1241 |
| His | His | Ala | Val | His | Val | Asn | Val | Ser | Gly | Glu | Thr | Thr | Gly | Tyr | Tyr | |
| | | | 930 | | | | | 935 | | | | | 940 | | | |
| AGC | GAC | TTC | GAC | TCG | CTC | GGA | GCC | CTC | GCC | AAG | GTC | CTG | CGT | GAC | GGG | 1289 |
| Ser | Asp | Phe | Asp | Ser | Leu | Gly | Ala | Leu | Ala | Lys | Val | Leu | Arg | Asp | Gly | |
| | | 945 | | | | | 950 | | | | | 955 | | | | |
| TTC | TTC | CAC | GAC | GGC | AGC | TAC | TCC | AGC | TTC | CGC | GGC | CGC | TGC | CAC | GGC | 1337 |
| Phe | Phe | His | Asp | Gly | Ser | Tyr | Ser | Ser | Phe | Arg | Gly | Arg | Cys | His | Gly | |
| | 960 | | | | | 965 | | | | | 970 | | | | | |
| CGG | CCG | ATC | AAC | TTC | AGC | GCC | GTG | CAT | CCG | GCC | GCG | CTG | GTG | GTC | TGC | 1385 |
| Arg | Pro | Ile | Asn | Phe | Ser | Ala | Val | His | Pro | Ala | Ala | Leu | Val | Val | Cys | |
| 975 | | | | | 980 | | | | | 985 | | | | | 990 | |
| TCA | CAG | AAC | CAT | GAC | CAG | ATC | GGC | AAC | CGG | GCC | ACC | GGG | GAC | CGG | CTG | 1433 |
| Ser | Gln | Asn | His | Asp | Gln | Ile | Gly | Asn | Arg | Ala | Thr | Gly | Asp | Arg | Leu | |
| | | | 995 | | | | | 1000 | | | | | 1005 | | | |

| | | | | | | | | | | | | | | | | |
|---|---|---|---|---|---|---|---|---|---|---|---|---|---|---|---|---|
| TCC | CAG | TCA | CTT | CCG | TAC | GGC | AGC | CTG | GCC | CTG | GCC | GCC | GTG | CTG | ACC | 1481 |
| Ser | Gln | Ser | Leu | Pro | Tyr | Gly | Ser | Leu | Ala | Leu | Ala | Ala | Val | Leu | Thr | |
| | | 1010 | | | | | 1015 | | | | | 1020 | | | | |
| CTC | ACC | GGT | CCG | TTC | ACG | CCC | ATG | CTG | TTC | ATG | GGA | GAG | GAA | TAC | GGG | 1529 |
| Leu | Thr | Gly | Pro | Phe | Thr | Pro | Met | Leu | Phe | Met | Gly | Glu | Glu | Tyr | Gly | |
| | 1025 | | | | | 1030 | | | | | 1035 | | | | | |
| GCC | ACC | ACC | CCG | TGG | CAG | TTC | TTC | ACC | TCG | CAC | CCT | GAA | CCC | GAG | CTG | 1577 |
| Ala | Thr | Thr | Pro | Trp | Gln | Phe | Phe | Thr | Ser | His | Pro | Glu | Pro | Glu | Leu | |
| | 1040 | | | | | 1045 | | | | | 1050 | | | | | |
| GGC | AAG | GCC | ACG | GCC | GAG | GGC | AGG | ATC | AGG | GAG | TTC | GAG | CGC | ATG | GGG | 1625 |
| Gly | Lys | Ala | Thr | Ala | Glu | Gly | Arg | Ile | Arg | Glu | Phe | Glu | Arg | Met | Gly | |
| 1055 | | | | | 1060 | | | | | 1065 | | | | | 1070 | |
| TGG | GAT | CCC | GCC | GTC | GTG | CCC | GAT | CCG | CAG | GAT | CCG | GAG | ACC | TTC | ACC | 1673 |
| Trp | Asp | Pro | Ala | Val | Val | Pro | Asp | Pro | Gln | Asp | Pro | Glu | Thr | Phe | Thr | |
| | | | | 1075 | | | | | 1080 | | | | | 1085 | | |
| CGC | TCC | AAA | CTG | GAC | TGG | GCG | GAA | GCG | TCC | GCC | GGC | GAT | CAT | GCC | CGC | 1721 |
| Arg | Ser | Lys | Leu | Asp | Trp | Ala | Glu | Ala | Ser | Ala | Gly | Asp | His | Ala | Arg | |
| | | | 1090 | | | | | 1095 | | | | | 1100 | | | |
| CTC | CTG | GAG | CTG | TAC | CGC | TCG | CTT | ATC | ACG | CTG | CGG | CGG | TCA | ACT | CCG | 1769 |
| Leu | Leu | Glu | Leu | Tyr | Arg | Ser | Leu | Ile | Thr | Leu | Arg | Arg | Ser | Thr | Pro | |
| | | 1105 | | | | | 1110 | | | | | 1115 | | | | |
| GAG | CTC | GCG | CGC | CTG | GGC | TTT | GCG | GAC | ACC | GCC | GTC | GAG | TTC | GAC | GAC | 1817 |
| Glu | Leu | Ala | Arg | Leu | Gly | Phe | Ala | Asp | Thr | Ala | Val | Glu | Phe | Asp | Asp | |
| | 1120 | | | | | 1125 | | | | | 1130 | | | | | |
| GAC | GCC | CGC | TGG | CTC | CGT | TAT | TGG | CGC | GGA | GGC | GTG | CAG | GTG | GTG | CTG | 1865 |
| Asp | Ala | Arg | Trp | Leu | Arg | Tyr | Trp | Arg | Gly | Gly | Val | Gln | Val | Val | Leu | |
| 1135 | | | | | 1140 | | | | | 1145 | | | | | 1150 | |
| AAC | TTC | GCG | GAC | CGT | CCC | ATC | AGC | CTG | GAC | CGG | CCG | GGA | ACC | GCG | CTG | 1913 |
| Asn | Phe | Ala | Asp | Arg | Pro | Ile | Ser | Leu | Asp | Arg | Pro | Gly | Thr | Ala | Leu | |
| | | | | 1155 | | | | | 1160 | | | | | 1165 | | |
| CTG | CTC | GCC | ACC | GAC | GAC | GCC | GTC | CGG | ATG | GAC | GGA | GTC | CAG | GTG | GAG | 1961 |
| Leu | Leu | Ala | Thr | Asp | Asp | Ala | Val | Arg | Met | Asp | Gly | Val | Gln | Val | Glu | |
| | | | 1170 | | | | | 1175 | | | | | 1180 | | | |
| CTG | CCG | CCG | CTG | AGC | GCC | GCG | GTT | CTG | CGC | GAC | TGAGCGTGCG | | CGCCTTCGGG | | | 2014 |
| Leu | Pro | Pro | Leu | Ser | Ala | Ala | Val | Leu | Arg | Asp | | | | | | |
| | | 1185 | | | | | 1190 | | | | | | | | | |

| | | | |
|---|---|---|---|
| GCGGGCGTCC TTCCGGTGAC CGGATGCTGG ACGCCCGCCC CGCAGCTCCA CAGGCGCTGG | | | 2074 |
| CAGGATGGAA CGTATGACTT TTCTGGCAGC GGACAACCGC TACGAAACCA TGCCATACCG | | | 2134 |
| CCGCGTCGGA CGCAGCGGGC TGAAGCT | | | 2161 |

( 2 ) INFORMATION FOR SEQ ID NO:12:

( i ) SEQUENCE CHARACTERISTICS:
        ( A ) LENGTH: 596 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

| | | | | | | | | | | | | | | |
|---|---|---|---|---|---|---|---|---|---|---|---|---|---|---|
| Met | Thr | Gln | Pro | Asn | Asp | Ala | Ala | Lys | Pro | Val | Gln | Gly | Ala | Gly | Arg |
| 1 | | | | 5 | | | | | 10 | | | | | 15 | |
| Phe | Asp | Ile | Trp | Ala | Pro | Glu | Ala | Gly | Thr | Val | Thr | Leu | Leu | Ala | Gly |
| | | | 20 | | | | | 25 | | | | | 30 | | |
| Gly | Glu | Arg | Tyr | Glu | Met | Gly | Arg | Arg | Pro | Gly | Asn | Gly | Pro | Ala | Asp |
| | | 35 | | | | | 40 | | | | | 45 | | | |
| Glu | Gly | Trp | Trp | Thr | Ala | Ala | Asp | Ala | Pro | Thr | Gly | Ala | Asp | Val | Asp |
| | 50 | | | | | 55 | | | | | 60 | | | | |
| Tyr | Gly | Tyr | Leu | Leu | Asp | Gly | Asp | Glu | Ile | Pro | Leu | Pro | Asp | Pro | Arg |

```
           65                       70                      75                        80

Thr  Arg  Arg  Gln  Pro  Glu  Gly  Val  His  Ala  Leu  Ser  Arg  Thr  Phe  Asp
                    85                  90                       95

Pro  Gly  Ala  His  Arg  Trp  Gln  Asp  Ala  Gly  Trp  Gln  Gly  Arg  Glu  Leu
               100                 105                 110

Gln  Gly  Ser  Val  Ile  Tyr  Glu  Leu  His  Ile  Gly  Thr  Phe  Thr  Pro  Glu
          115                 120                      125

Gly  Thr  Leu  Asp  Ala  Ala  Ala  Gly  Lys  Leu  Asp  Tyr  Leu  Ala  Gly  Leu
     130                 135                      140

Gly  Ile  Asp  Phe  Ile  Glu  Leu  Leu  Pro  Val  Asn  Ala  Phe  Asn  Gly  Thr
145                      150                 155                           160

His  Asn  Trp  Gly  Tyr  Asp  Gly  Val  Gln  Trp  Phe  Ala  Val  His  Glu  Gly
                    165                 170                      175

Tyr  Gly  Gly  Pro  Ala  Ala  Tyr  Gln  Arg  Phe  Val  Asp  Ala  Ala  His  Ala
               180                 185                      190

Ala  Gly  Leu  Gly  Val  Ile  Gln  Asp  Val  Val  Tyr  Asn  His  Leu  Gly  Pro
          195                 200                 205

Ser  Gly  Asn  Tyr  Leu  Pro  Arg  Tyr  Gly  Pro  Tyr  Leu  Lys  His  Gly  Glu
     210                 215                      220

Gly  Asn  Thr  Trp  Gly  Asp  Ser  Val  Asn  Leu  Asp  Gly  Pro  Gly  Ser  Asp
225                      230                 235                           240

His  Val  Arg  Gln  Tyr  Ile  Leu  Asp  Asn  Val  Ala  Met  Trp  Leu  Arg  Asp
                    245                 250                      255

Tyr  Arg  Val  Asp  Gly  Leu  Arg  Leu  Asp  Ala  Val  His  Ala  Leu  Lys  Asp
               260                 265                      270

Glu  Arg  Ala  Val  His  Ile  Leu  Glu  Glu  Phe  Gly  Ala  Leu  Ala  Asp  Ala
          275                 280                      285

Leu  Ser  Ser  Glu  Gly  Gly  Arg  Pro  Leu  Thr  Leu  Ile  Ala  Glu  Ser  Asp
     290                 295                      300

Leu  Asn  Asn  Pro  Arg  Leu  Leu  Tyr  Pro  Arg  Asp  Val  Asn  Gly  Tyr  Gly
305                      310                 315                           320

Leu  Ala  Gly  Gln  Trp  Ser  Asp  Asp  Phe  His  His  Ala  Val  His  Val  Asn
                    325                 330                      335

Val  Ser  Gly  Glu  Thr  Thr  Gly  Tyr  Tyr  Ser  Asp  Phe  Asp  Ser  Leu  Gly
               340                 345                      350

Ala  Leu  Ala  Lys  Val  Leu  Arg  Asp  Gly  Phe  Phe  His  Asp  Gly  Ser  Tyr
          355                 360                      365

Ser  Ser  Phe  Arg  Gly  Arg  Cys  His  Gly  Arg  Pro  Ile  Asn  Phe  Ser  Ala
     370                 375                      380

Val  His  Pro  Ala  Ala  Leu  Val  Val  Cys  Ser  Gln  Asn  His  Asp  Gln  Ile
385                      390                 395                           400

Gly  Asn  Arg  Ala  Thr  Gly  Asp  Arg  Leu  Ser  Gln  Ser  Leu  Pro  Tyr  Gly
                    405                 410                      415

Ser  Leu  Ala  Leu  Ala  Ala  Val  Leu  Thr  Leu  Thr  Gly  Pro  Phe  Thr  Pro
               420                 425                      430

Met  Leu  Phe  Met  Gly  Glu  Glu  Tyr  Gly  Ala  Thr  Thr  Pro  Trp  Gln  Phe
          435                 440                      445

Phe  Thr  Ser  His  Pro  Glu  Pro  Glu  Leu  Gly  Lys  Ala  Thr  Ala  Glu  Gly
     450                 455                      460

Arg  Ile  Arg  Glu  Phe  Glu  Arg  Met  Gly  Trp  Asp  Pro  Ala  Val  Val  Pro
465                      470                 475                           480

Asp  Pro  Gln  Asp  Pro  Glu  Thr  Phe  Thr  Arg  Ser  Lys  Leu  Asp  Trp  Ala
                    485                 490                      495
```

| Glu | Ala | Ser | Ala  | Gly | Asp | His | Ala | Arg  | Leu | Leu | Glu | Leu  | Tyr | Arg | Ser |
|-----|-----|-----|------|-----|-----|-----|-----|------|-----|-----|-----|------|-----|-----|-----|
|     |     |     | 500  |     |     |     |     | 505  |     |     |     | 510  |     |     |     |

| Leu | Ile | Thr | Leu | Arg | Arg | Ser | Thr | Pro | Glu | Leu | Ala | Arg | Leu | Gly | Phe |
|-----|-----|-----|-----|-----|-----|-----|-----|-----|-----|-----|-----|-----|-----|-----|-----|
|     |     | 515 |     |     |     |     | 520 |     |     |     |     | 525 |     |     |     |

| Ala | Asp | Thr | Ala | Val | Glu | Phe | Asp | Asp | Ala | Arg | Trp | Leu | Arg | Tyr |
|-----|-----|-----|-----|-----|-----|-----|-----|-----|-----|-----|-----|-----|-----|-----|
|     | 530 |     |     |     |     | 535 |     |     |     | 540 |     |     |     |     |

| Trp | Arg | Gly | Gly | Val | Gln | Val | Val | Leu | Asn | Phe | Ala | Asp | Arg | Pro | Ile |
|-----|-----|-----|-----|-----|-----|-----|-----|-----|-----|-----|-----|-----|-----|-----|-----|
| 545 |     |     |     |     | 550 |     |     |     |     | 555 |     |     |     |     | 560 |

| Ser | Leu | Asp | Arg | Pro | Gly | Thr | Ala | Leu | Leu | Leu | Ala | Thr | Asp | Asp | Ala |
|-----|-----|-----|-----|-----|-----|-----|-----|-----|-----|-----|-----|-----|-----|-----|-----|
|     |     |     |     | 565 |     |     |     |     | 570 |     |     |     | 575 |     |     |

| Val | Arg | Met | Asp | Gly | Val | Gln | Val | Glu | Leu | Pro | Pro | Leu | Ser | Ala | Ala |
|-----|-----|-----|-----|-----|-----|-----|-----|-----|-----|-----|-----|-----|-----|-----|-----|
|     |     |     | 580 |     |     |     |     | 585 |     |     |     |     | 590 |     |     |

| Val | Leu | Arg | Asp |
|-----|-----|-----|-----|
|     |     | 595 |     |

( 2 ) INFORMATION FOR SEQ ID NO:13:

( i ) SEQUENCE CHARACTERISTICS:
        ( A ) LENGTH: 2056 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 90..1883

( x i ) SEQUENCE DESCRIPTION: SEQ ID NO:13:

```
GCCGGCTTCG  GACCGGGGGC  AGTGAAGATC  GCCGACATCT  TCCGGTCGTT  CCCCGTTGCG        60

CTGCTGGTGC  CGCAGACAGG  AGGAGAGTC   ATG ACG CAC ACC TAC CCG CGG GAA          113
                                    Met Thr His Thr Tyr Pro Arg Glu
                                        600

GCC GCG AAA CCC GTC CTG GGC CCC GCA CGC TAC GAC GTC TGG GCG CCC              161
Ala Ala Lys Pro Val Leu Gly Pro Ala Arg Tyr Asp Val Trp Ala Pro
605              610                 615                 620

AAC GCT GAA TCC GTG ACG CTG CTG GCC GGC GGG GAG CGC TAC GCC ATG              209
Asn Ala Glu Ser Val Thr Leu Leu Ala Gly Gly Glu Arg Tyr Ala Met
                625                 630                 635

CAG CGC CGG GCC GAG ACC GGG CCG GAG GAC GCC GGC TGG TGG ACC GCC              257
Gln Arg Arg Ala Glu Thr Gly Pro Glu Asp Ala Gly Trp Trp Thr Ala
            640                 645                 650

GCC GGC GCG CCT ACG GAT GGC AAC GTG GAC TAC GGG TAC CTT CTG GAC              305
Ala Gly Ala Pro Thr Asp Gly Asn Val Asp Tyr Gly Tyr Leu Leu Asp
        655                 660                 665

GGC GAC GAA ACA CCG CTT CCG GAT CCA CGG ACC CGC CGC CAG CCC GAC              353
Gly Asp Glu Thr Pro Leu Pro Asp Pro Arg Thr Arg Arg Gln Pro Asp
    670                 675                 680

GGC GTC CAC GGC CTG TCC CGC ACG TTC GAC CCG TCC GCG TAC AGC TGG              401
Gly Val His Ala Leu Ser Arg Thr Phe Asp Pro Ser Ala Tyr Ser Trp
685                 690                 695                 700

CAG GAC GAC GCC TGG CAG GGC AGG GAA CTG CAG GGC GCC GTC ATC TAC              449
Gln Asp Asp Ala Trp Gln Gly Arg Glu Leu Gln Gly Ala Val Ile Tyr
                705                 710                 715

GAG CTC CAC CTC GGA ACA TTC ACG CCC GAA GGG ACG CTG GAG GCG GCC              497
Glu Leu His Leu Gly Thr Phe Thr Pro Glu Gly Thr Leu Glu Ala Ala
            720                 725                 730

GCC GGA AAG CTG GAC TAC CTC GCC GGC TTG GGC GTC GAC TTC ATC GAG              545
Ala Gly Lys Leu Asp Tyr Leu Ala Gly Leu Gly Val Asp Phe Ile Glu
        735                 740                 745
```

| | | | | | | | | | | | | | | | | |
|---|---|---|---|---|---|---|---|---|---|---|---|---|---|---|---|---|
| CTG | CTG | CCG | GTG | AAC | GCT | TTC | AAC | GGC | ACG | CAC | AAC | TGG | GGT | TAC | GAC | 593 |
| Leu | Leu | Pro | Val | Asn | Ala | Phe | Asn | Gly | Thr | His | Asn | Trp | Gly | Tyr | Asp | |
| | 750 | | | | 755 | | | | | 760 | | | | | | |
| GGT | GTC | CAG | TGG | TTC | GCT | GTG | CAC | GAG | GCA | TAC | GGC | GGG | CCG | GAA | GCG | 641 |
| Gly | Val | Gln | Trp | Phe | Ala | Val | His | Glu | Ala | Tyr | Gly | Gly | Pro | Glu | Ala | |
| 765 | | | | 770 | | | | | 775 | | | | | | 780 | |
| TAC | CAG | CGG | TTC | GTC | GAC | GCC | GCC | CAC | GCC | GCA | GGC | CTT | GGC | GTG | ATC | 689 |
| Tyr | Gln | Arg | Phe | Val | Asp | Ala | Ala | His | Ala | Ala | Gly | Leu | Gly | Val | Ile | |
| | | | | 785 | | | | 790 | | | | | | 795 | | |
| CAG | GAC | GTG | GTC | TAC | AAC | CAC | CTC | GGC | CCC | AGC | GGG | AAC | TAC | CTG | CCG | 737 |
| Gln | Asp | Val | Val | Tyr | Asn | His | Leu | Gly | Pro | Ser | Gly | Asn | Tyr | Leu | Pro | |
| | | | 800 | | | | 805 | | | | | | 810 | | | |
| CGG | TTC | GGG | CCG | TAC | CTC | AAG | CAG | GGC | GAG | GGT | AAC | ACG | TGG | GGC | GAC | 785 |
| Arg | Phe | Gly | Pro | Tyr | Leu | Lys | Gln | Gly | Glu | Gly | Asn | Thr | Trp | Gly | Asp | |
| | | 815 | | | | | 820 | | | | | 825 | | | | |
| TCG | GTG | AAC | CTG | GAC | GGG | CCC | GGC | TCC | GAC | CAT | GTG | CGC | CGG | TAC | ATC | 833 |
| Ser | Val | Asn | Leu | Asp | Gly | Pro | Gly | Ser | Asp | His | Val | Arg | Arg | Tyr | Ile | |
| | 830 | | | | | 835 | | | | | | 840 | | | | |
| CTG | GAC | AAC | CTG | GCC | ATG | TGG | CTG | CGT | GAC | TAC | CGG | GTG | GAC | GGC | CTG | 881 |
| Leu | Asp | Asn | Leu | Ala | Met | Trp | Leu | Arg | Asp | Tyr | Arg | Val | Asp | Gly | Leu | |
| 845 | | | | | 850 | | | | | 855 | | | | | 860 | |
| CGG | CTG | GAC | GCC | GTC | CAC | GCC | CTG | AAG | GAT | GAG | CGG | GCG | GTG | CAC | ATC | 929 |
| Arg | Leu | Asp | Ala | Val | His | Ala | Leu | Lys | Asp | Glu | Arg | Ala | Val | His | Ile | |
| | | | | 865 | | | | 870 | | | | | | 875 | | |
| CTG | GAG | GAC | TTC | GGG | GCG | CTG | GCC | GAT | CAG | ATC | TCC | GCC | GAG | GTG | GGA | 977 |
| Leu | Glu | Asp | Phe | Gly | Ala | Leu | Ala | Asp | Gln | Ile | Ser | Ala | Glu | Val | Gly | |
| | | | 880 | | | | | 885 | | | | | 890 | | | |
| CGG | CCG | CTG | ACG | CTC | ATC | GCC | GAG | TCC | GAC | CTC | AAC | AAC | CCG | CGG | CTG | 1025 |
| Arg | Pro | Leu | Thr | Leu | Ile | Ala | Glu | Ser | Asp | Leu | Asn | Asn | Pro | Arg | Leu | |
| | | 895 | | | | | 900 | | | | | 905 | | | | |
| CTG | TAC | CCG | CGG | GAC | GTC | AAC | GGG | TAC | GGG | CTG | GAA | GGG | CAG | TGG | AGC | 1073 |
| Leu | Tyr | Pro | Arg | Asp | Val | Asn | Gly | Tyr | Gly | Leu | Glu | Gly | Gln | Trp | Ser | |
| | 910 | | | | | 915 | | | | | 920 | | | | | |
| GAC | GAC | TTC | CAC | CAC | GCC | GTC | CAC | GTC | AAC | GTC | ACC | GGC | GAA | ACC | ACC | 1121 |
| Asp | Asp | Phe | His | His | Ala | Val | His | Val | Asn | Val | Thr | Gly | Glu | Thr | Thr | |
| 925 | | | | | 930 | | | | | 935 | | | | | 940 | |
| GGC | TAC | TAC | AGT | GAC | TTC | GAC | TCG | CTG | GCC | GCC | CTC | GCC | AAG | GTG | CTC | 1169 |
| Gly | Tyr | Tyr | Ser | Asp | Phe | Asp | Ser | Leu | Ala | Ala | Leu | Ala | Lys | Val | Leu | |
| | | | | 945 | | | | | 950 | | | | | 955 | | |
| CGG | GAC | GGC | TTC | TTC | CAC | GAC | GGC | AGC | TAC | TCC | AGC | TTC | CGG | GAA | CGC | 1217 |
| Arg | Asp | Gly | Phe | Phe | His | Asp | Gly | Ser | Tyr | Ser | Ser | Phe | Arg | Glu | Arg | |
| | | | 960 | | | | | 965 | | | | | 970 | | | |
| CAC | CAC | GGA | CGG | CCG | ATT | AAT | TTC | AGC | GCC | GTA | CAC | CCA | GCC | GCC | CTG | 1265 |
| His | His | Gly | Arg | Pro | Ile | Asn | Phe | Ser | Ala | Val | His | Pro | Ala | Ala | Leu | |
| | | | 975 | | | | | 980 | | | | | 985 | | | |
| GTG | GTC | TGT | TCG | CAG | AAC | CAC | GAC | CAG | ATC | GGC | AAC | CGT | GCC | ACG | GGG | 1313 |
| Val | Val | Cys | Ser | Gln | Asn | His | Asp | Gln | Ile | Gly | Asn | Arg | Ala | Thr | Gly | |
| | 990 | | | | | 995 | | | | | 1000 | | | | | |
| GAC | CGG | CTC | TCC | CAG | ACC | CTG | CCG | TAC | GGA | AGC | CTG | GCC | CTC | GCT | GCG | 1361 |
| Asp | Arg | Leu | Ser | Gln | Thr | Leu | Pro | Tyr | Gly | Ser | Leu | Ala | Leu | Ala | Ala | |
| 1005 | | | | | 1010 | | | | | 1015 | | | | | 1020 | |
| GTG | CTG | ACC | CTG | ACG | GGA | CCC | TTC | ACG | CCC | ATG | CTG | CTC | ATG | GGC | GAG | 1409 |
| Val | Leu | Thr | Leu | Thr | Gly | Pro | Phe | Thr | Pro | Met | Leu | Leu | Met | Gly | Glu | |
| | | | | 1025 | | | | | 1030 | | | | | 1035 | | |
| GAG | TAC | GGC | GCC | AGC | ACG | CCG | TGG | CAG | TTT | TTC | ACC | TCG | CAC | CCG | GAG | 1457 |
| Glu | Tyr | Gly | Ala | Ser | Thr | Pro | Trp | Gln | Phe | Phe | Thr | Ser | His | Pro | Glu | |
| | | | | 1040 | | | | | 1045 | | | | | 1050 | | |
| CCG | GAG | CTC | GGC | AAG | GCC | ACC | GCG | GAG | GGC | CGG | ATC | AAG | GAG | TTC | GAG | 1505 |
| Pro | Glu | Leu | Gly | Lys | Ala | Thr | Ala | Glu | Gly | Arg | Ile | Lys | Glu | Phe | Glu | |
| | | | | 1055 | | | | | 1060 | | | | | 1065 | | |

```
CGC ATG GGG TGG GAT CCC GCC GTC GTG CCC GAT CCC CAG GAT CCT GAG        1553
Arg Met Gly Trp Asp Pro Ala Val Val Pro Asp Pro Gln Asp Pro Glu
        1070            1075            1080

ACG TTC CGC CGG TCC AAG CTG GAC TGG GCG GAA GCC GCC GAA GGC GAC        1601
Thr Phe Arg Arg Ser Lys Leu Asp Trp Ala Glu Ala Ala Glu Gly Asp
1085            1090            1095                    1100

CAT GCC CGG CTG CTG GAG CTG TAC CGT TCG CTC ACC GCC CTG CGC CGC        1649
His Ala Arg Leu Leu Glu Leu Tyr Arg Ser Leu Thr Ala Leu Arg Arg
                1105            1110                1115

TCC ACG CCG GAC CTC ACC AAG CTG GGC TTC GAG GAC ACG CAG GTG GCG        1697
Ser Thr Pro Asp Leu Thr Lys Leu Gly Phe Glu Asp Thr Gln Val Ala
            1120            1125            1130

TTC GAC GAG GAC GCC CGC TGG CTG CGG TTC CGC CGG GGT GGC GTG CAG        1745
Phe Asp Glu Asp Ala Arg Trp Leu Arg Phe Arg Arg Gly Gly Val Gln
        1135            1140            1145

GTG CTG CTC AAC TTC TCG GAA CAG CCC GTG AGC CTG GAC GGG GCG GGC        1793
Val Leu Leu Asn Phe Ser Glu Gln Pro Val Ser Leu Asp Gly Ala Gly
    1150            1155            1160

ACG GCC CTG CTG CTG GCC ACC GAC GAC GCC GTC CGG CTA GAA GGT GAG        1841
Thr Ala Leu Leu Leu Ala Thr Asp Asp Ala Val Arg Leu Glu Gly Glu
1165            1170            1175            1180

CGT GCG GAA CTC GGT CCG CTG AGC GCC GCC GTC GTC AGC GAC                1883
Arg Ala Glu Leu Gly Pro Leu Ser Ala Ala Val Val Ser Asp
                1185            1190

TGACGTTTTC TTGGGGGCGG CGTCCACCGC CGGTGACCGG ATGGTGGACG TCCGCCCCGA      1943

AGCCTCGGCG CGGCTGGCAG GATGGAACGC ATGACTTATG TGGCCTCGGA CACCCGCTAC      2003

GACACCATGC CCTACCGCCG CGTCGGACGC AGCGGCCTCA AACTGCCGGC CAT             2056
```

( 2 ) INFORMATION FOR SEQ ID NO:14:

( i ) SEQUENCE CHARACTERISTICS:
        ( A ) LENGTH: 598 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

```
Met Thr His Thr Tyr Pro Arg Glu Ala Ala Lys Pro Val Leu Gly Pro
 1               5                  10                  15

Ala Arg Tyr Asp Val Trp Ala Pro Asn Ala Glu Ser Val Thr Leu Leu
            20                  25                  30

Ala Gly Gly Glu Arg Tyr Ala Met Gln Arg Arg Ala Glu Thr Gly Pro
        35                  40                  45

Glu Asp Ala Gly Trp Trp Thr Ala Ala Gly Ala Pro Thr Asp Gly Asn
    50                  55                  60

Val Asp Tyr Gly Tyr Leu Leu Asp Gly Asp Glu Thr Pro Leu Pro Asp
65                  70                  75                  80

Pro Arg Thr Arg Arg Gln Pro Asp Gly Val His Ala Leu Ser Arg Thr
                85                  90                  95

Phe Asp Pro Ser Ala Tyr Ser Trp Gln Asp Ala Trp Gln Gly Arg
            100                 105                 110

Glu Leu Gln Gly Ala Val Ile Tyr Glu Leu His Leu Gly Thr Phe Thr
        115                 120                 125

Pro Glu Gly Thr Leu Glu Ala Ala Ala Gly Lys Leu Asp Tyr Leu Ala
    130                 135                 140

Gly Leu Gly Val Asp Phe Ile Glu Leu Leu Pro Val Asn Ala Phe Asn
145                 150                 155                 160
```

```
Gly Thr His Asn Trp Gly Tyr Asp Gly Val Gln Trp Phe Ala Val His
            165             170                 175

Glu Ala Tyr Gly Gly Pro Glu Ala Tyr Gln Arg Phe Val Asp Ala Ala
            180             185                 190

His Ala Ala Gly Leu Gly Val Ile Gln Asp Val Val Tyr Asn His Leu
            195             200                 205

Gly Pro Ser Gly Asn Tyr Leu Pro Arg Phe Gly Pro Tyr Leu Lys Gln
    210             215                 220

Gly Glu Gly Asn Thr Trp Gly Asp Ser Val Asn Leu Asp Gly Pro Gly
225             230                 235                     240

Ser Asp His Val Arg Arg Tyr Ile Leu Asp Asn Leu Ala Met Trp Leu
            245             250                 255

Arg Asp Tyr Arg Val Asp Gly Leu Arg Leu Asp Ala Val His Ala Leu
            260             265                 270

Lys Asp Glu Arg Ala Val His Ile Leu Glu Asp Phe Gly Ala Leu Ala
            275             280                 285

Asp Gln Ile Ser Ala Glu Val Gly Arg Pro Leu Thr Leu Ile Ala Glu
    290             295                 300

Ser Asp Leu Asn Asn Pro Arg Leu Leu Tyr Pro Arg Asp Val Asn Gly
305             310                 315                     320

Tyr Gly Leu Glu Gly Gln Trp Ser Asp Asp Phe His His Ala Val His
            325             330                 335

Val Asn Val Thr Gly Glu Thr Thr Gly Tyr Tyr Ser Asp Phe Asp Ser
            340             345                 350

Leu Ala Ala Leu Ala Lys Val Leu Arg Asp Gly Phe Phe His Asp Gly
            355             360                 365

Ser Tyr Ser Ser Phe Arg Glu Arg His His Gly Arg Pro Ile Asn Phe
    370             375                 380

Ser Ala Val His Pro Ala Ala Leu Val Val Cys Ser Gln Asn His Asp
385             390                 395                     400

Gln Ile Gly Asn Arg Ala Thr Gly Asp Arg Leu Ser Gln Thr Leu Pro
            405             410                 415

Tyr Gly Ser Leu Ala Leu Ala Ala Val Leu Thr Leu Thr Gly Pro Phe
            420             425                 430

Thr Pro Met Leu Leu Met Gly Glu Glu Tyr Gly Ala Ser Thr Pro Trp
            435             440                 445

Gln Phe Phe Thr Ser His Pro Glu Pro Glu Leu Gly Lys Ala Thr Ala
    450             455                 460

Glu Gly Arg Ile Lys Glu Phe Glu Arg Met Gly Trp Asp Pro Ala Val
465             470                 475                     480

Val Pro Asp Pro Gln Asp Pro Glu Thr Phe Arg Arg Ser Lys Leu Asp
            485             490                 495

Trp Ala Glu Ala Ala Glu Gly Asp His Ala Arg Leu Leu Glu Leu Tyr
            500             505                 510

Arg Ser Leu Thr Ala Leu Arg Arg Ser Thr Pro Asp Leu Thr Lys Leu
    515             520                 525

Gly Phe Glu Asp Thr Gln Val Ala Phe Asp Glu Asp Ala Arg Trp Leu
    530             535                 540

Arg Phe Arg Arg Gly Gly Val Gln Val Leu Leu Asn Phe Ser Glu Gln
545             550                 555                     560

Pro Val Ser Leu Asp Gly Ala Gly Thr Ala Leu Leu Leu Ala Thr Asp
            565             570                 575

Asp Ala Val Arg Leu Glu Gly Glu Arg Ala Glu Leu Gly Pro Leu Ser
            580             585                 590
```

Ala Ala Val Val Ser Asp
595

( 2 ) INFORMATION FOR SEQ ID NO:15:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

TTYGAYATHT GGGCNCC         17

( 2 ) INFORMATION FOR SEQ ID NO:16:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

GTAAAACGAC GGCCAGT         17

( 2 ) INFORMATION FOR SEQ ID NO:17:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

ATGGGNTGGG AYCCNGC         17

( 2 ) INFORMATION FOR SEQ ID NO:18:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:18:

TAYGAYGTNT GGGC         14

DNA ENCODING ENZYME, RECOMBINANT DNA AND ENZYME, TRANSFORMANT, AND THEIR PREPARATIONS AND USES

BACKGROUND OF THE INVENTION

1. Field of the Invention

The present invention relates to a novel DNA encoding an enzyme which releases trehalose from non-reducing saccharides having a trehalose structure as an end unit and having a degree of glucose polymerization of 3 or higher, recombinant DNA containing the same, and a transformant, and further relates to a recombinant enzyme which releases trehalose from non-reducing saccharides having a trehalose structure as an end unit and having a degree of glucose polymerization of 3 or higher, as well as to preparations and uses thereof.

2. Description of the Prior Art

Trehalose is a disaccharide which consists of 2 glucose molecules which are linked together with their reducing groups, and, naturally, it is present in bacteria, fungi, algae, insects, etc., in an extremely small quantity. Having no reducing residue within the molecule, trehalose does not cause an unsatisfactory browning reaction even when heated in the presence of amino acids or the like, and because of this it can sweeten food products without fear of causing unsatisfactory coloration and deterioration. Trehalose, however, is far from being readily prepared in a desired amount by conventional methods, and, actually, it has not scarcely been used for sweetening food products.

Conventional methods are roughly classified into 2 groups, i.e. the one using cells of microorganisms and the other employing a multi-enzymatic system wherein enzymes are allowed to act on saccharides. The former, as disclosed in Japanese Patent Laid-Open No. 154,485/75, is a method which comprises allowing to grow microorganisms such as bacteria and yeasts in a nutrient culture medium, and collecting trehalose from the proliferated cells in the resultant culture. The latter, as disclosed in Japanese Patent Laid-Open No. 216,695/83, is a method which comprises providing maltose as a substrate, allowing a multi-enzymatic system using maltose- and trehalose-phosphorylases to act on maltose, and isolating the formed trehalose from the reaction system. Although the former facilitates the growth of microorganisms with a relative easiness, it requires a sequentially-complicated step for collecting trehalose from the microorganisms which contain at most 15 w/w % trehalose, on a dry solid basis (d.s.b.). While the latter enables the separation of trehalose itself with a relative easiness, but it is theoretically difficult to increase the trehalose yield by allowing enzymes to act on substrates at a considerably-high concentration because the enzymatic reaction per se is an equilibrium reaction of 2 different types of enzymes and the equilibrium point constantly inclines to the side of forming glucose phosphate.

In view of the foregoing, the present inventors energetically screened enzymes which form saccharides having a trehalose structure from amylaceous saccharides, and found that microorganisms such as those of the spices Rhizobium sp. M-11 and arthrobacter sp. Q36 produce an absolutely novel enzyme which forms non-reducing saccharides having a trehalose structure as an end unit from reducing amylaceous saccharides having a degree of glucose polymerization of 3 or higher. Before or after this finding, it was revealed that such non-reducing saccharides are almost quantitatively hydrolyzed into trehalose and glucose and/or maltooligosaccharides by other enzymes produced from the same microorganisms of the species Rhizobium sp. M-11 and Arthrobacter sp. Q36. Since the combination use of such enzymes enables to form a desired amount of trehalose with a relative easiness, the aforementioned objects relating to trehalose would be completely overcome. Insufficient producibility of such enzymes by the microorganisms results in a drawback that a relatively-large scale culture of the microorganisms is inevitable to industrially produce trehalose and/or non-reducing saccharides having a trehalose structure as an end unit.

Recombinant DNA technology has made a remarkable progress in recent years. At present, even an enzyme, whose total amino acid sequence has not yet been revealed, can be readily prepared in a desired amount, if a gene encoding the enzyme was once isolated and the base sequence was decoded, by preparing a recombinant DNA containing a DNA which encodes the enzyme, introducing the recombinant DNA into microorganisms or cells of plants or animals, and culturing the resultant transformants. Under these circumstances, urgently required are the finding of genes which encode these enzymes and the elucidation of their base sequences.

SUMMARY OF THE INVENTION

It is an object of the present invention to provide a DNA which encodes an enzyme that releases trehalose from non-reducing saccharides having a trehalose structure as an end unit.

It is a further object of the present invention to provide a replicable recombinant DNA containing the aforesaid DNA.

It is yet another object of the present invention to provide a transformant which is prepared by introducing the recombinant DNA into an appropriate host.

It is a further object of the present invention to prepare the aforesaid enzyme by the application of the recombinant DNA technology.

It is a further object of the present invention to provide a preparation of the enzyme.

It is a further object of the present invention to provide a method for converting non-reducing saccharides having a trehalose structure as an end unit and having a degree of glucose polymerization of 3 or higher.

The first object of the present invention is attained by a DNA which encodes an enzyme that releases trehalose from non-reducing saccharides having a trehalose structure as an end unit and having a degree of glucose polymerization of 3 or higher.

The second object of the present invention is attained by a replicable recombinant DNA which contains the aforesaid DNA and a self-replicable vector.

The third object of the present invention is attained by a transformant prepared by introducing the aforesaid self-replicable vector into an appropriate host.

The fourth object of the present invention is attained by a recombinant enzyme which releases trehalose from non-reducing saccharides having a trehalose structure as an end unit and having a degree of glucose polymerization of 3 or higher.

The fifth object of the present invention is attained by a process to produce the recombinant enzyme comprising culturing a transformant capable of forming the enzyme in a nutrient culture medium, and recovering the formed enzyme from the resultant culture.

The sixth object of the present invention is attained by a method for converting non-reducing saccharides containing a step of allowing the recombinant enzyme to act on non-reducing saccharides, having a trehalose structure as an end unit and having a degree of glucose polymerization of 3 or higher, to release trehalose from the saccharides.

BRIEF DESCRIPTION OF THE ACCOMPANYING DRAWINGS

Figure 9:
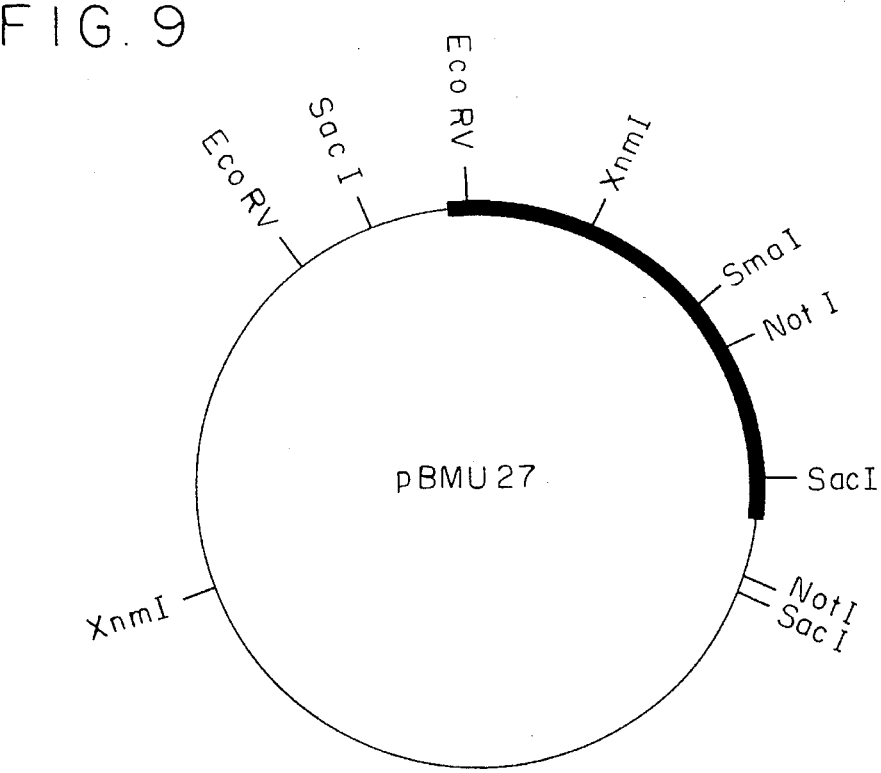

FIG. 9 shows the restriction map of the recombinant DNA pBMU27 according to the present invention. In the figure, the bold-lined part is a DNA encoding an enzyme derived from Rhizobium sp. M-11.

Figure 10:
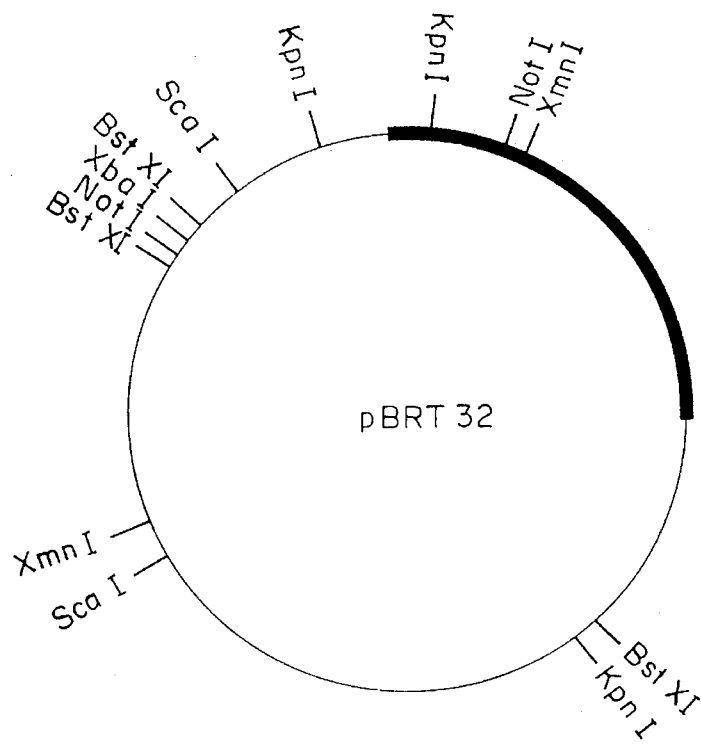

FIG. 10 shows the restriction map of the recombinant DNA pBRT32 according to the present invention. In the figure, the bold-lined part is a DNA encoding an enzyme derived from arthrobacter sp. Q36.

DETAILED DESCRIPTION OF THE INVENTION

The DNA according to the present invention exerts the production of the enzyme encoded by the DNA in a manner that the DNA is inserted into an appropriate self-replicable vector to form a replicable recombinant DNA, followed by introducing the recombinant DNA into a host, incapable of producing the enzyme per se but readily replicable, to form a transformant.

Although the recombinant DNA per se does not produce the enzyme, the production of the enzyme encoded by the DNA is attained by introducing the recombinant DNA into a host, incapable of producing the enzyme but replicable with a relative easiness, to form a transformant, and culturing the transformant to produce the enzyme.

The transformant according to the present invention produces the enzyme when cultured.

The recombinant enzyme according to the present invention releases trehalose when acts on non-reducing saccharides having a trehalose structure as an end unit and having a degree of glucose polymerization of 3 or higher.

The recombinant enzyme is readily obtained in a desired amount by culturing the transformant according to the invention.

Non-reducing saccharides having a trehalose structure as an end unit and having a degree of glucose polymerization of 3 or higher are converted into trehalose and glucose and/or maltooligosaccharides.

The present invention is based on the finding of a novel enzyme which releases trehalose from non-reducing saccharides having a trehalose structure as an end unit and having a degree of glucose polymerization of 3 or higher. Such an enzyme can be obtained from cultures of microorganisms of the species Rhizobium sp. M-11 and Arthrobacter sp. Q36, and the present inventors isolated the enzyme by the combination use of conventional purification methods using column chromatography mainly, examined the properties and features, and revealed the reality, i.e. it is a polypeptide having the following physicochemical properties:

(1) Action

Releasing trehalose from non-reducing saccharides having a trehalose structure as an end unit and having a degree of glucose polymerization of 3 or higher;

(2) Molecular weight

About 57,000–68,000 daltons on sodium dodecyl sulfate polyacrylamide gel electrophoresis (SDS-PAGE );

(3) Isoelectric point

About 3.3–4.6 on isoelectrophoresis;

(4) Optimum temperature

Exhibiting an optimum temperature of around 35°–45° C. when incubated at pH 7.0 for 30 min;

(5) Optimum pH

Exhibiting an optimum pH of around 6.0–7.5 when incubated at 40° C. for 30 min;

(6) Thermal stability

Stable up to a temperature of around 30°–45° C. when incubated at pH 7.0 for 60 min; and (7) pH Stability Stable up to a pH of around 5.5–10.0 when incubated at 25° C. for 16 hours.

Experiments, which were conducted to reveal the physicochemical properties of the enzymes produced by microorganisms of the species Rhizobiumsp. M-11 and Arthrobacter sp. Q36 (the enzymes from Rhizobium sp. M-11 and Arthrobacter sp. Q36 are respectively designated as "enzyme M-11" and "enzyme Q36" hereinafter), are explained in the below:

Experiment 1

Purification of enzyme

Experiment 1-1

Purification of enzyme M-11

In 500-ml Erlenmeyer flasks were placed 100 ml aliquots of a liquid culture medium (pH 7.0) containing 2.0 w/v % "PINE-DEX #4", a starch hydrolysate commercialized by Matsutani Chemical Ind., Co., Ltd., Tokyo, Japan, 0.5 w/v % peptone, 0.1 w/v % yeast extract, 0.1 w/v % disodium hydrogen phosphate, and 0.1 w/v % potassium dihydrogen phosphate, and the flasks were autoclaved at 120° C. for 20 min to effect sterilization. After cooling the flasks a seed culture of Rhizobium sp. M-11 was inoculated into each liquid culture medium in each flask, followed by the incubation at 27° C. for 24 hours under rotary-shaking conditions. Twenty L of a fresh preparation of the same liquid culture medium was put in a 30-L jar fermentor and sterilized, followed by inoculating one v/v % of the culture obtained in the above into the sterilized liquid culture medium in the jar fermentor, and incubating it at a pH of 6–8 and 30° C. for 24 hours under aeration-agitation conditions.

Thereafter, about 18 L of the resultant culture was subjected to an ultra-high pressure cell disrupting apparatus to disrupt cells. The resultant suspension was centrifuged to obtain a supernatant, and to about 16 L of which was added ammonium sulfate to give a 20 w/v % saturation, followed by the standing at 4° C. for one hour and the centrifugation to remove sediment. To the resultant supernatant was added ammonium sulfate to give a 60 w/v % saturation, and the solution was allowed to stand at 4° C. for 24 hours and centrifuged to collect sediment which was then dissolved in a minimum amount of 10 mM phosphate buffer (pH 7.0). The solution thus obtained was dialyzed against 10 mM phosphate buffer (pH 7.0) for 24 hours, and centrifuged to remove insoluble substances. The resultant supernatant was fed to a column packed with "DEAE-TOYOPEARL®", a product for ion-exchange chromatography commercialized by Tosoh Corporation, Tokyo, Japan, which had been previously equilibrated with 10 mM phosphate buffer (pH 7.0), followed by feeding to the column a linear gradient buffer of sodium chloride ranging from 0M to 0.5M in 10 mM phosphate buffer (pH 7.0). Fractions containing the objective enzyme were collected from the eluate, pooled, dialyzed for 10 hours against 50 mM phosphate buffer (pH 7.0) containing 2M ammonium sulfate, and centrifuged to remove insoluble substances. Thereafter, the resultant supernatant was fed to a column, which had been packed with "BUTYL TOYOPEARL®", a gel for hydrophobic column chromatography commercialized by Tosoh Corporation, Tokyo, Japan, and equilibrated with 50 mM phosphate buffer (pH 7.0) containing 2M ammonium sulfate, followed by feeding to the column a linear gradient buffer of ammonium sulfate ranging from 2M to 0M in 50mM phosphate buffer (pH 7.0). Fractions containing the objective enzyme were collected from the eluate, pooled, fed to a column packed with "TOYOPEARL® HW-55", a product for gel filtration column chromatography commercialized by Tosoh Corporation, Tokyo, Japan, which had been previously equilibrated with 50 mM phosphate buffer (pH 7.0), followed by feeding to the column 50 mM phosphate buffer (pH 7.0) and collecting fractions containing the objective enzyme. The enzyme thus obtained had a specific activity of about 240 units/mg protein, and the yield was about 650 units per L of the culture.

Throughout the specification the enzyme activity is expressed by the value measured on the following assay: Place 4 ml of 50 mM phosphate buffer (pH 7.0) containing 1.25 w/v % maltotriosyltrehalose in a test tube, add one ml of an enzyme solution to the tube, and incubate the resultant solution at 40° C. for 30 min to effect enzymatic reaction. Thereafter, one ml of the reaction mixture is mixed with 2 ml of copper reagent to suspend the enzymatic reaction, followed by assaying the reducing activity by the Somogyi-Nelson's method. As a control, an enzyme, which has been previously inactivated by heating at 100° C. for 10 min, is similarly treated as above. One unit activity of the enzyme is defined as the amount of enzyme which increases the reducing power corresponding to one μmol glucose per min under the above conditions.

Experiment 1-2

Purification of enzyme Q36

Similarly as in Experiment 1-1, a seed culture of Arthrobacter sp. Q36 was cultured, and the resultant culture was treated to obtain a purified enzyme Q36 having a specific activity of about 450 units/mg protein in a yield of about 650 units per L of the culture.

Experiment 2

Physicochemical property of enzyme

Experiment 2-1

Action

According to the method disclosed in Japanese Patent Application No. 349,216/93, a non-reducing saccharide containing 98 w/w % or higher, d.s.b., α-glucosyltrehalose, α-maltosyltrehalose, α-maltotriosyltrehalose, α-maltotetraosyltrehalose or α-maltopentaosyltrehalose. Either of the non-reducing saccharides as a substrate was dissolved in 50 mM phosphate buffer (pH 7.0) into a 20 w/v % solution which was then mixed with 2 units/g substrate of the purified enzyme M-11 or Q36 in Experiment 1 and subjected to an enzymatic reaction at 40° C. for 48 hours. The reaction mixture was desalted in usual manner, fed to "WB-T-330", a column for high-performance liquid chromatography (HPLC) commercialized by Wako Pure Chemical Industries, Ltd., Tokyo, Japan, followed by feeding to the column distilled water at a flow rate of 0.5 ml/min at ambient temperature to isolate saccharides contained in the reaction mixture while monitoring the saccharide concentration of the eluate with "MODEL RI-8012", a differential refractometer commercialized by Tosoh Corporation, Tokyo, Japan. As a control, an aqueous solution which contains either maltotriose, maltotetraose, maltopentaose, maltohexaose or maltoheptaose was similarly treated as above, and the resultant mixture was analyzed. The saccharide compositions of the reaction mixtures were tabulated in Tables 1 and 2.

TABLE 1

| Substrate | Saccharide in reaction mixture | Saccharide composition (%) |
| --- | --- | --- |
| α-Glucosyltrehalose | Trehalose | 17.5 |
| | Glucose | 6.5 |
| | α-Glucosyltrehalose | 76.0 |
| α-Maltosyltrehalose | Trehalose | 44.3 |
| | Maltose | 44.4 |
| | α-Maltosyltrehalose | 11.3 |
| α-Maltotriosyltrehalose | Trehalose | 39.5 |
| | Maltotriose | 60.0 |
| | α-Maltotriosyltrehalose | 0.5 |
| α-Maltotetraosyltrehalose | Trehalose | 34.2 |
| | Maltotetraose | 65.5 |
| | α-Maltotetraosyltrehalose | 0.3 |
| α-Maltopentaosyltrehalose | Trehalose | 29.1 |
| | Maltopentaose | 70.6 |
| | α-Maltopentaosyltrehalose | 0.3 |
| Maltotriose | Maltotriose | 100.0 |
| Maltotetraose | Maltotetraose | 100.0 |
| Maltopentaose | Maltopentaose | 100.0 |
| Maltohexaose | Maltohexaose | 100.0 |
| Maltoheptaose | Maltoheptaose | 100.0 |

TABLE 2

| Substrate | Saccharide in reaction mixture | Saccharide composition (%) |
| --- | --- | --- |
| α-Glucosyltrehalose | Trehalose | 19.3 |
| | Glucose | 10.2 |
| | α-Glucosyltrehalose | 70.5 |
| α-Maltosyltrehalose | Trehalose | 44.5 |
| | Maltose | 44.4 |

TABLE 2-continued

| Substrate | Saccharide in reaction mixture | Saccharide composition (%) |
|---|---|---|
| α-Maltotriosyltrehalose | α-Maltosyltrehalose | 11.1 |
| | Trehalose | 38.8 |
| | Maltotriose | 60.7 |
| | α-Maltotriosyltrehalose | 0.5 |
| α-Maltotetraosyltre- halose | Trehalose | 34.1 |
| | Maltotetraose | 65.7 |
| | α-Maltotetraosyltrehalose | 0.2 |
| α-Maltopentaosyltre- halose | Trehalose | 29.3 |
| | Maltopentaose | 70.4 |
| | α-Maltopentaosyltrehalose | 0.3 |
| Maltotriose | Maltotriose | 100.0 |
| Maltotetraose | Maltotetraose | 100.0 |
| Maltopentaose | Maltopentaose | 100.0 |
| Maltohexaose | Maltohexaose | 100.0 |
| Maltoheptaose | Maltoheptaose | 100.0 |

As shown in Tables 1 and 2, enzymes M-11 and Q36 almost quantitatively released trehalose, glucose and maltooligosaccharides from non-reducing saccharides having a trehalose structure as an end unit and having a degree of glucose polymerization of 3 or higher. These enzymes did not act on maltooligosaccharides, as a substrate, having a degree of glucose polymerization of 3 or higher. These facts indicate that these enzymes selectively act on non-reducing saccharides having a trehalose structure as an end unit and having a degree of polymerization degree of 3 or higher, and specifically hydrolyze the glycosidic bond between trehalose- and glycosyl-residues. Such an enzyme has never been reported and is estimated to have a novel enzymatic reaction mechanism.

Experiment 2-2

Molecular weight

In accordance with the method reported by U. K. Laemmli in Nature, Vol. 227, pp. 680–685 (1970), the purified enzymes M-11 and Q36 in Experiment 1 were respectively electrophoresed on sodium dodecyl sulfate polyacrylamide gel electrophoresis to show a single protein band at a position corresponding to about 57,000–68,000 daltons. The marker proteins used in this experiment were myosin (MW= 200,000 daltons), β-galactosidase (MW=116,250 daltons), phosphorylase B (MW=97,400 daltons), serum albumin (MW=66,200 daltons) and ovalbumin (MW=45,000 daltons).

Experiment 2-3

Isoelectric point

The purified enzymes M-11 and Q36 obtained in Experiment 1 gave an isoelectric point of about 3.3–4.6 on isoelectrophoresis.

Experiment 2-4

Optimum temperature

Figure 1:
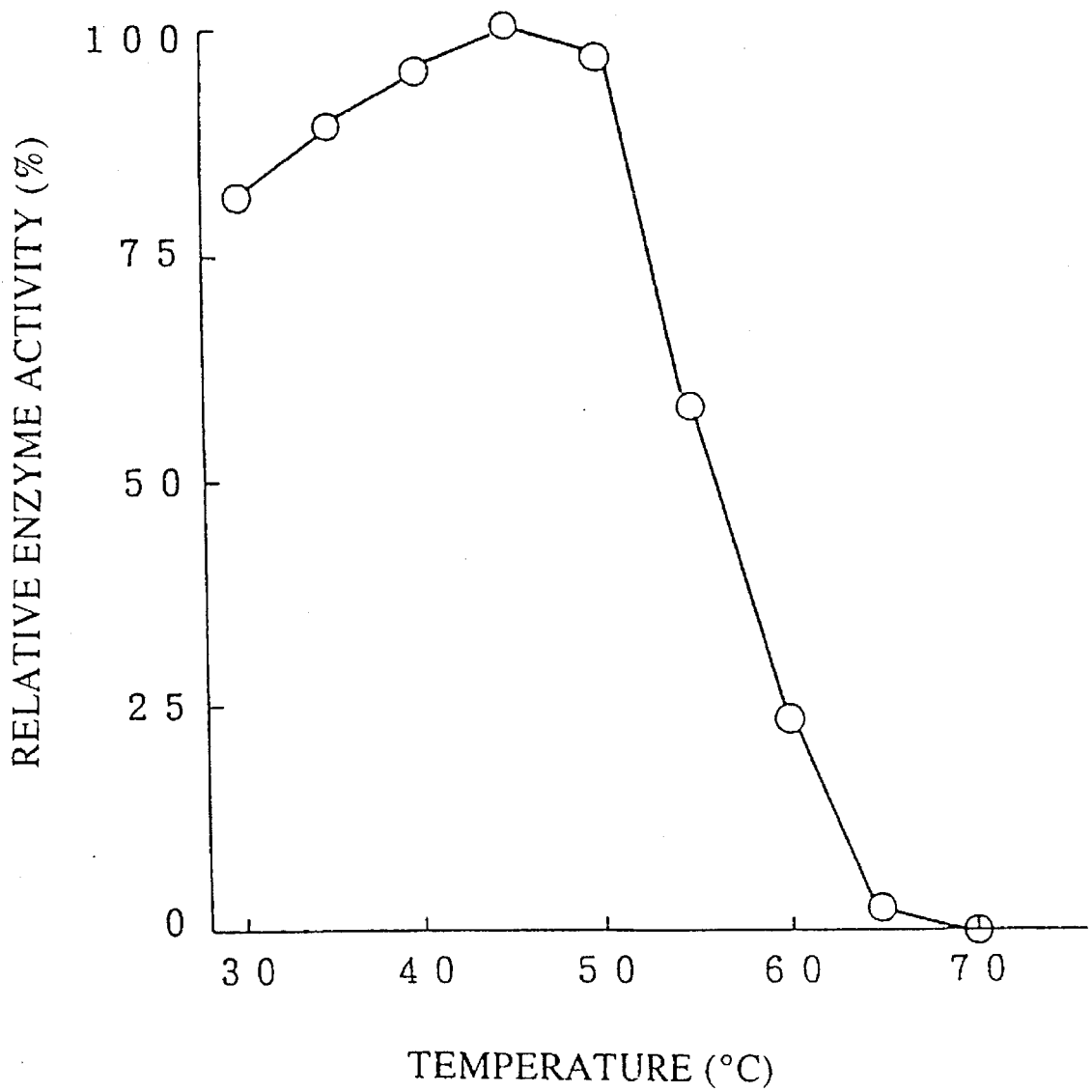
FIG. 1 shows the optimum temperature of an enzyme derived from Rhizobium sp. M-11.
Figure 2:
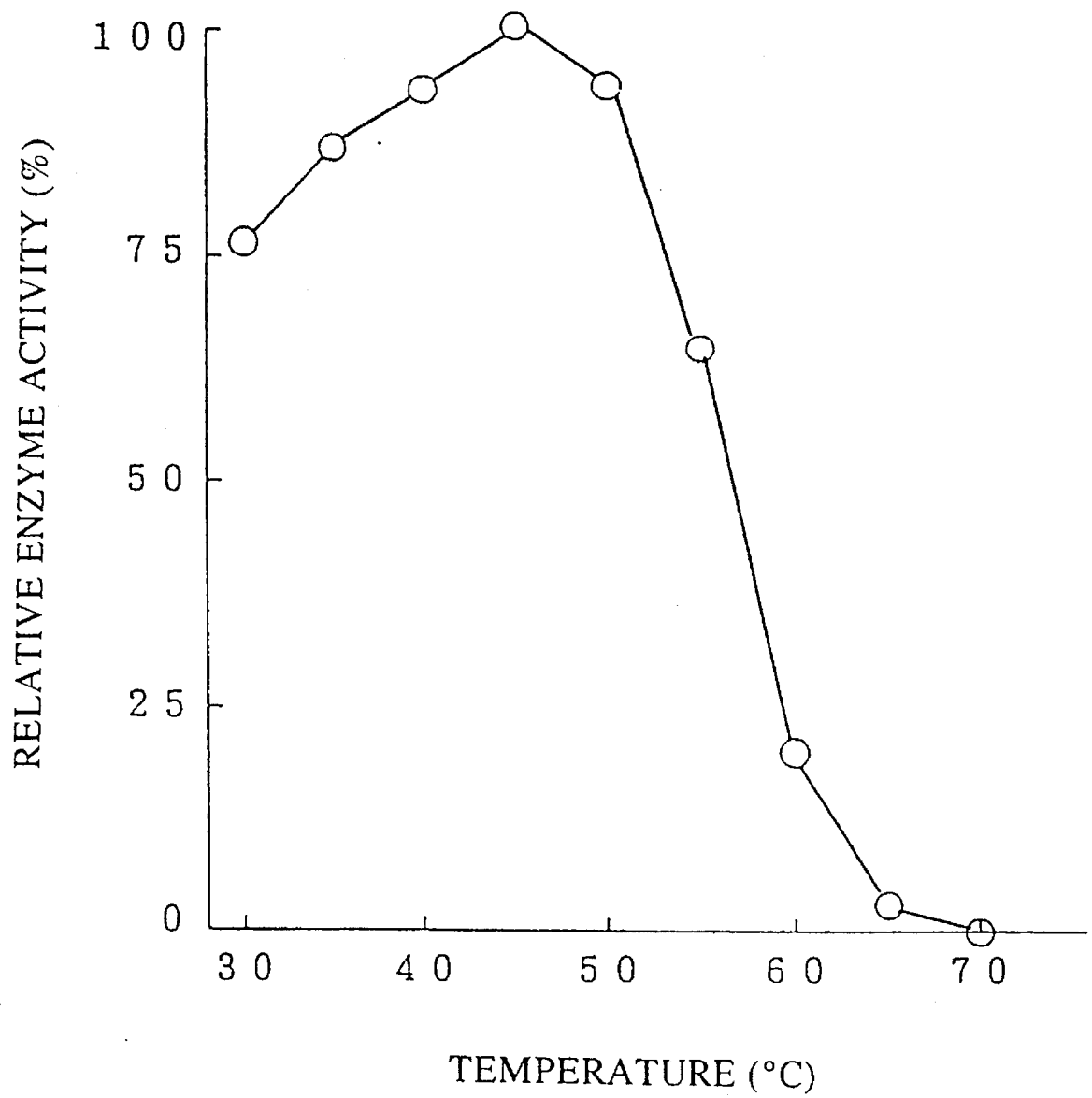
FIG. 2 shows the optimum temperature of an enzyme derived from Arthrobacter sp. Q36.

The optimum temperature of the purified enzymes M-11 and Q36 obtained in Experiment 1 was about 35°–45° C. as shown in FIGS. 1 and 2 when incubated in usual manner in 50 mM phosphate buffer (pH 7.0) for 30 min.

Experiment 2-5

Optimum pH

Figure 3:
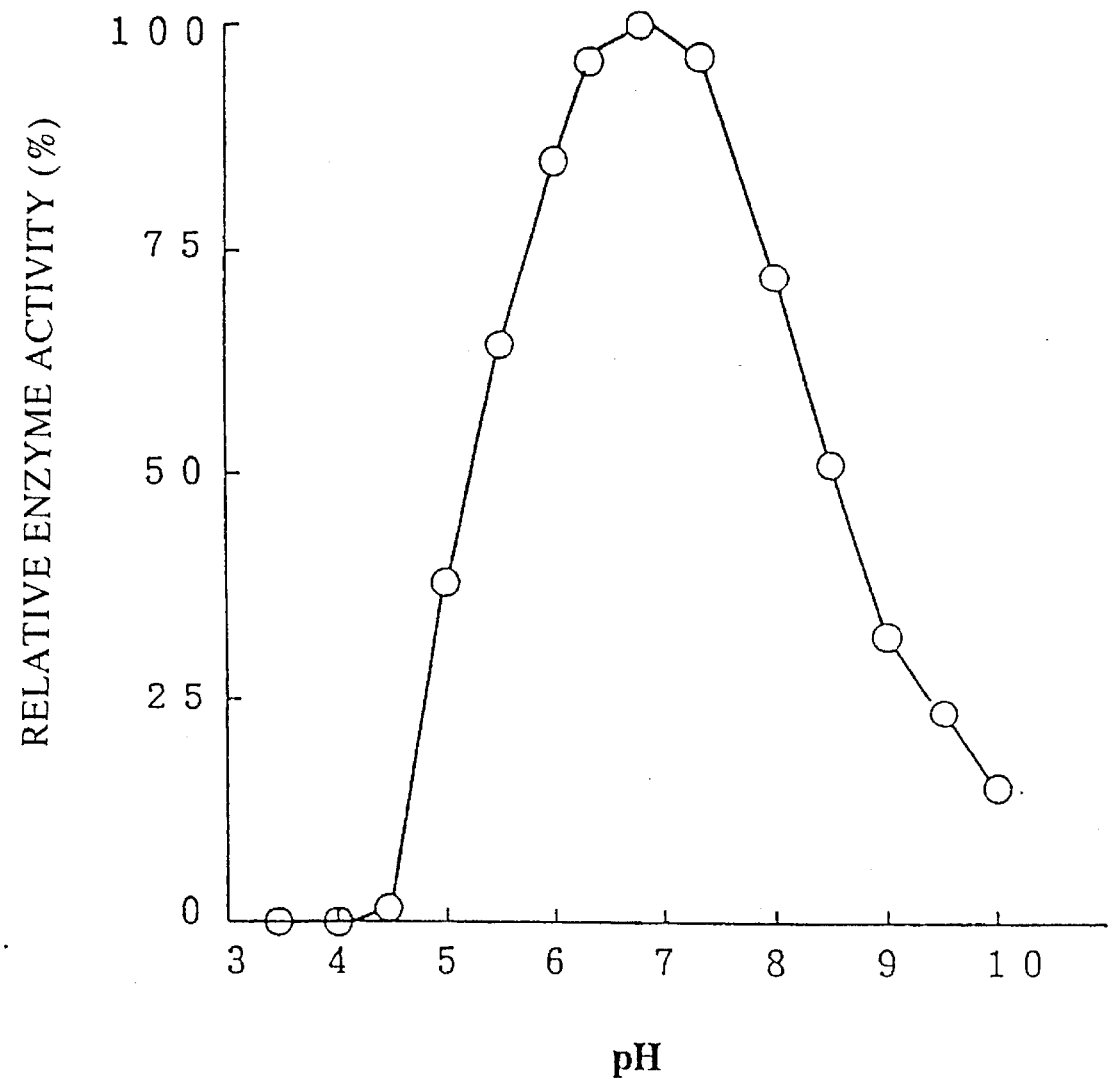
FIG. 3 shows the optimum pH of an enzyme derived from Rhizobium sp. M-11.
Figure 4:
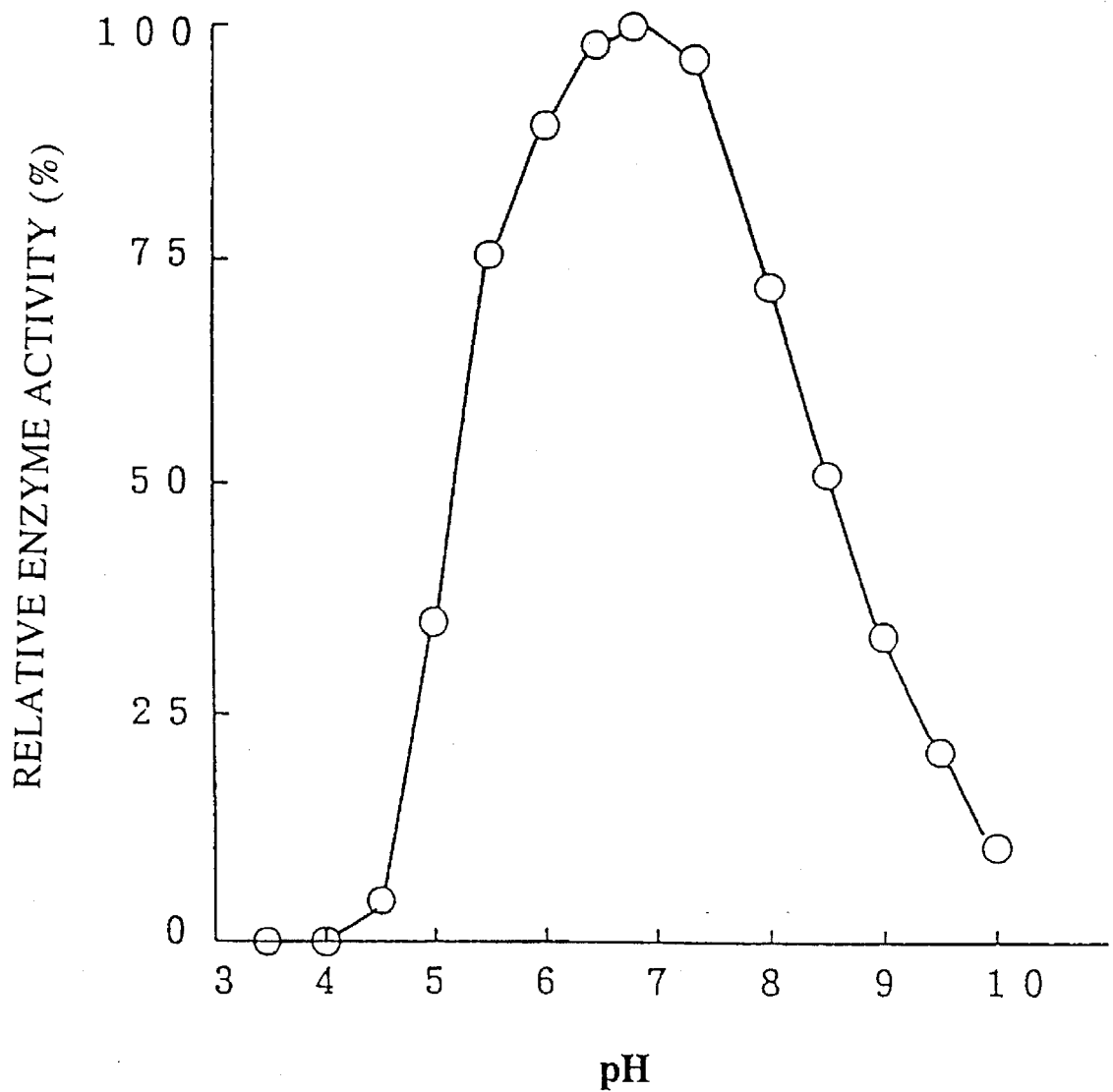
FIG. 4 shows the optimum pH of an enzyme derived from arthrobacter sp. Q36.

The optimum pH of the purified enzymes M-11 and Q36 obtained in Experiment 1 was about 6.0–7.5 as shown in FIGS. 3 and 4 when experimented in usual manner by incubating them at 40° C. for 30 min in 50 mM acetate buffer, phosphate buffer or sodium carbonate-sodium hydrogen carbonate buffer having different pHs.

Experiment 2-6

Thermal stability

Figure 5:
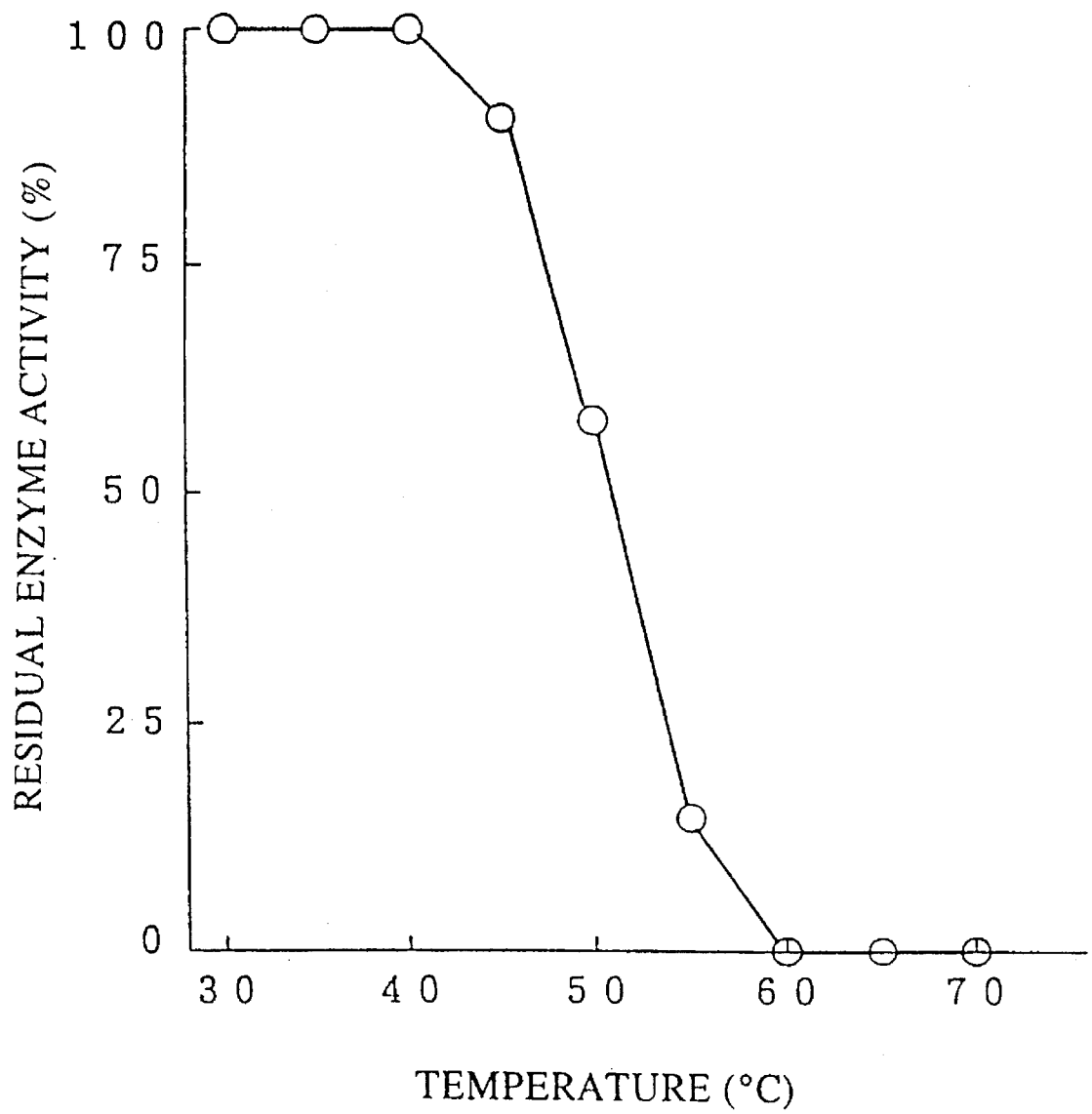
FIG. 5 shows the thermal stability of an enzyme derived from Rhizobium sp. M-11.
Figure 6:
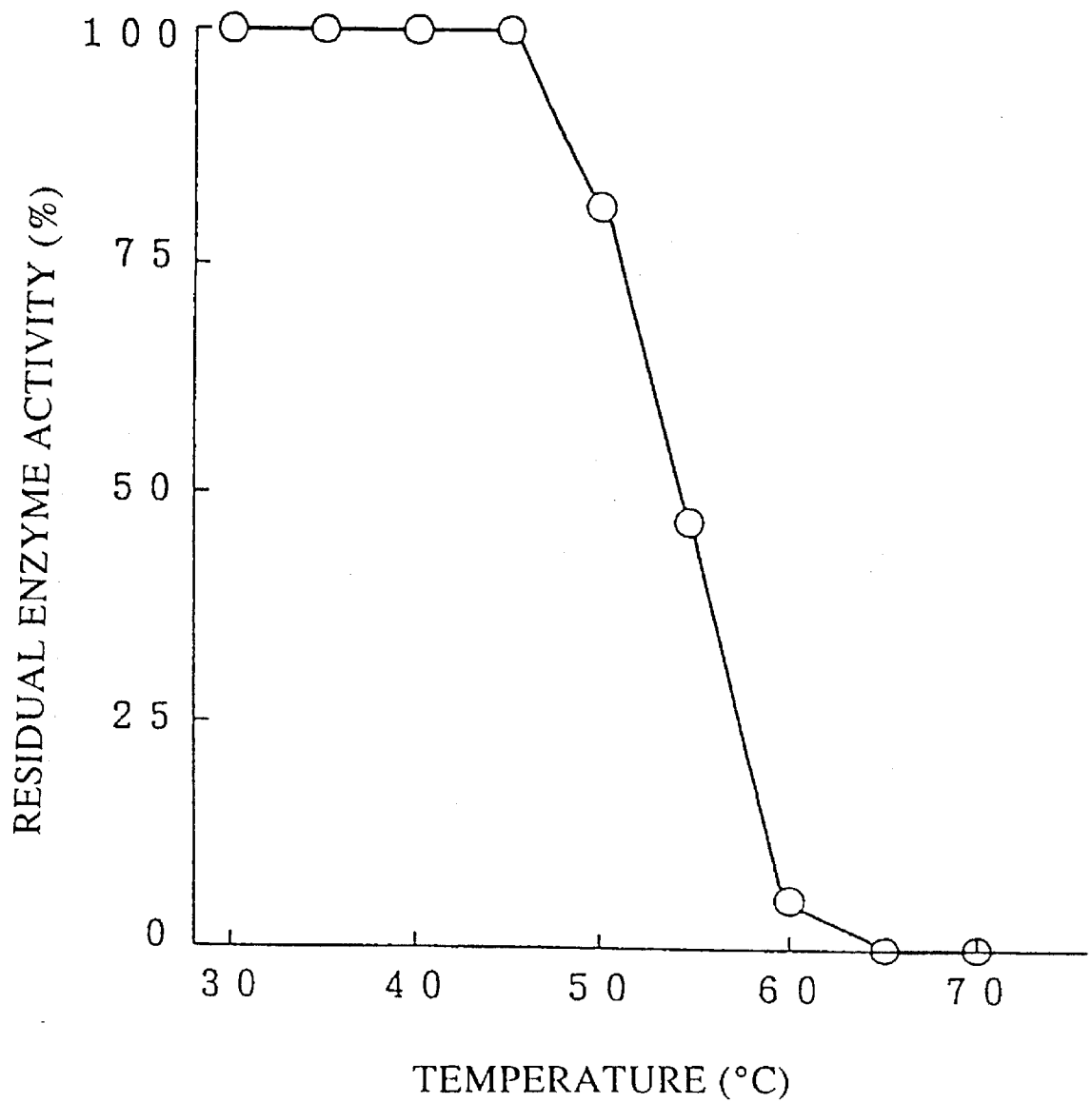
FIG. 6 shows the thermal stability of an enzyme derived from arthrobacter sp. Q36.

The purified enzymes M-11 and Q36 obtained in Experiment 1 were stable up to a temperature of about 30°–45° C. as shown in FIGS. 5 and 6 when experimented in usual manner by incubating them in 50 mM phosphate buffer (pH 7.0) for 60 min.

Experiment 2-7 pH Stability

Figure 7:
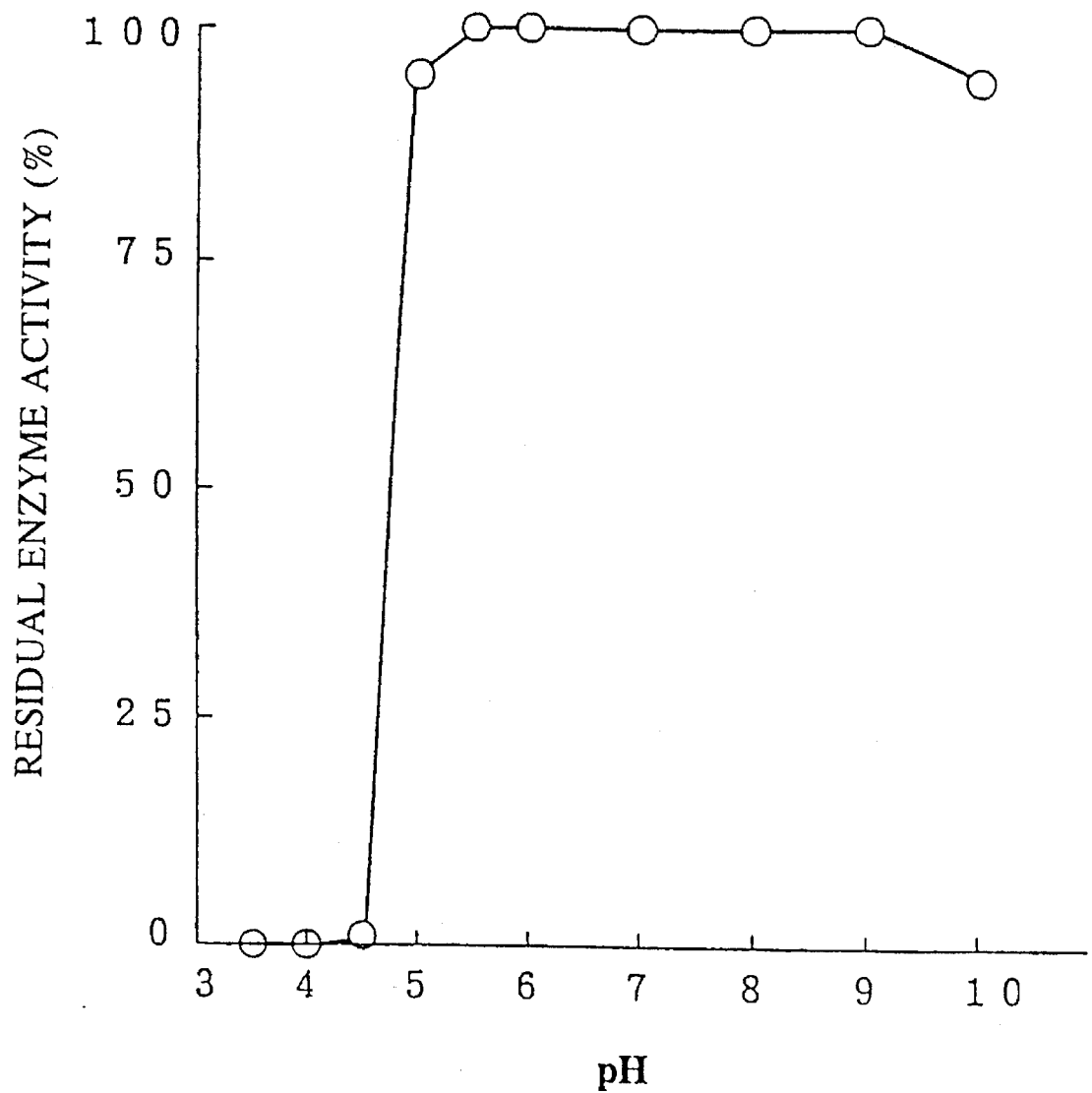
FIG. 7 shows the pH stability of an enzyme derived from Rhizobium sp. M-11.
Figure 8:
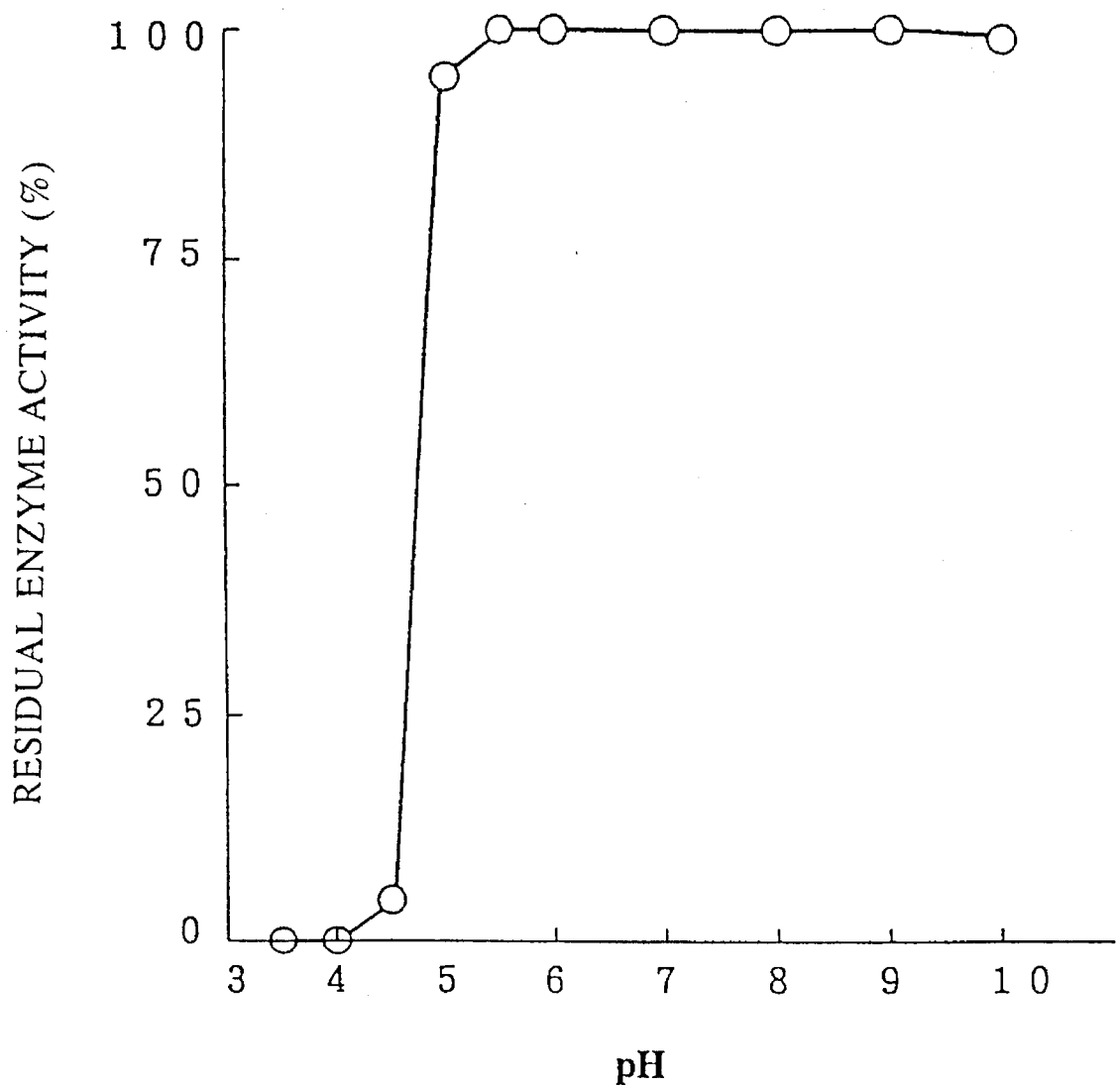
FIG. 8 shows the pH stability of an enzyme derived from Arthrobacter sp. Q36.

The purified enzymes M-11 and Q36 obtained in Experiment 1 were stable up to a pH of about 5.5–10.0 as shown in FIGS. 7 and 8 when experimented in usual manner by incubating them at 25° C. for 16 hours in 50 mM acetate buffer, phosphate buffer or sodium carbonate-sodium hydrogen carbonate buffer having different pHs.

Experiment 2-8

Amino acid sequence containing the N-terminal

The amino acid sequence containing the N-terminal of the purified enzyme M-11 obtained in Experiment 1 was analyzed on "MODEL 470A", a gas-phase protein sequencer commercialized by Applied Biosystems, Inc., Foster City, USA, to reveal that it has the amino acid sequence as shown in SEQ ID NO:5.

The amino acid sequence containing the N-terminal of the purified enzyme Q36 was analyzed similarly as above to reveal that it has the amino acid sequence as shown in SEQ ID NO:6.

Experiment 2-9

Partial amino acid sequence

An adequate amount of the purified enzyme M-11 obtained in Experiment 1-1 was weighed, dialyzed against 10 mM Tris-HCl buffer (pH 9.0) at 4° C. for 18 hours, and admixed with 10 mM Tris-HCl buffer (pH 9.0) to give a concentration of about one mg/ml of the enzyme. About one ml of the resultant solution was placed in a container, admixed with 10 μg lysyl endopeptidase, and incubated at 30° C. for 22 hours to partially hydrolyze the enzyme. The resultant hydrolysate was applied to "CAPCELL-PAK C18", a column for reverse-phase high-performance liquid chromatography commercialized by Shiseido Co., Ltd., Tokyo, Japan, which had been previously equilibrated with 0.1 v/v % trifluoroacetate containing 16 v/v % aqueous acetonitrile, followed by feeding to the column 0.1 v/v % trifluoroacetate at a flow rate of 0.9 ml/min while increasing the concentration of acetonitrile from 16 v/v % to 64 v/v % to separately collect fractions containing a peptide fragment eluted about 43 min or about 57 min after the initiation of feeding (the peptide fragments were respectively named "peptide fragment A" and "peptide fragment B"). Fractions containing the peptide fragment A or B were separately pooled, dried in vacuo, and dissolved in 0.1 v/v % trifluoroacetate containing 50 v/v % aqueous acetonitrile. Similarly as in Experiment 2-8, the peptide fragments A and B were analyzed to reveal that they have the amino acid sequences as shown in SEQ ID NOs:7 and 8, respectively.

Similarly as in enzyme M-11, enzyme Q36 obtained in Experiment 1-2 was partially hydrolyzed, and the resultant was fed to "μBONDAPAK C18", a column for reverse-phase high-performance liquid chromatography commercialized by Japan Millipore Ltd., Tokyo, Japan, which had been previously equilibrated with 0.1 v/v % trifluoroacetate containing 24 v/v % aqueous acetonitrile, followed by feeding to the column 0.1 v/v % trifluoroacetate containing 24 v/v % aqueous acetonitrile while increasing the concentration of aqueous acetonitrile from 24 v/v % to 44 v/v % at a flow rate of 0.9 ml/ml. Fractions containing a peptide fragment eluted about 4 min or about 24 min after the initiation of feeding (the fractions were respectively called "peptide fragment C" and "peptide fragment D" hereinafter) were respectively collected, pooled, dried in vacuo, and dissolved in 0.1 v/v % trifluoroacetate containing 50 v/v % aqueous acetonitrile. Analyses of the peptide fragments C and D conducted similarly as above have revealed that they have amino acid sequences as shown in SEQ ID NOs:9 10 respectively.

No enzyme having these physicochemical properties has been known, and this concluded that it is a novel substance. Referring to Rhizobium sp. M-11, it is a microorganism which was isolated from a soil of Okayama-city, Okayama, Japan, deposited on December 24, 1992, in National Institute of Bioscience and Human-Technology Agency of Industrial Science and Technology, Tsukuba, Ibaraki, Japan, and accepted under the accession number of FERM BP-4130, and it has been maintained by the institute. Arthrobacter sp. Q36 is a microorganism which was isolated from a soil of Soja-city, Okayama, Japan, deposited on June 3, 1993, in the same institute, and accepted under the accession number of FERM BP-4316, and it has been maintained by the institute. Japanese Patent Application No.340,343/93, applied by the same applicant, discloses the properties and features of the non-reducing saccharide-forming enzyme as well as the detailed bacteriological properties of these microorganisms.

The present inventors energetically screened the chromosomal DNA of Rhizobium sp. M-11 by using an oligonucleotide as a probe which had been chemically synthesized based on the partial amino acid sequence of enzyme M-11 as revealed in Experiment 2-8 or 2-9, and obtained a DNA fragment which consists of 1,767 base pairs having the base sequence as shown in the following SEQ ID NO:1 that initiates from the 5'-terminus. The decoding of the base sequence of the enzyme has revealed that it has an amino acid sequence consisting of 589 amino acids as shown in SEQ ID NO:2.

Similarly as in enzyme M-11, the chromosomal DNA of enzyme Q36 was screened by using an oligonucleotide as a probe which had been chemically synthesized based on a partial amino acid sequence of enzyme Q36, and this yielded a DNA fragment having a base sequence consisting of 1,791 base pairs as shown in SEQ ID NO:3. The base sequence was decoded to reveal that enzyme Q36 has an amino acid sequence consisting of 597 amino acids as shown in SEQ ID NO:4.

The sequential experimental steps used for revealing the base sequence and amino acid sequence as shown in SEQ ID NOs:1 to 4 are summarized as below:

(1) The enzyme was isolated from a culture of a donor microorganism and highly purified. The purified enzyme was partially hydrolyzed with protease, and the resultant 2 different types of peptide fragments were isolated and determined their amino acid sequences;

(2) Separately, a chromosomal DNA was isolated from a donor microorganism's cell, purified and partially digested by a restriction enzyme to obtain a DNA fragment consisting of about 2,000–6,000 base pairs. The DNA fragment was ligated by DNA ligase to a plasmid vector, which had been previously cut with a restriction enzyme, to obtain a recombinant DNA;

(3) The recombinant DNA was introduced into *Escherichia coli* to obtain transformants, and from which an objective transformant containing a DNA encoding the enzyme was selected by the colony hybridization method using an oligonucleotide, as a probe, which had been chemically synthesized based on the aforesaid partial amino acid sequence; and (4) The recombinant DNA was obtained from the selected transformant and annealed with a primer, followed by allowing a DNA polymerase to act on the resultant to extend the primer, and determining the base sequence of the resultant complementary chain DNA by the dideoxy chain termination method. The comparison of an amino acid sequence, estimable from the determined base sequence with the aforesaid amino acid sequence, confirmed that the base sequence encodes the enzyme.

The recombinant enzyme as referred to in the specification mean the whole recombinant enzymes which are preparable by the recombinant DNA technology and capable of releasing trehalose from non-reducing saccharides having a trehalose structure as an end unit and having a degree of glucose polymerization of 3 or higher. Generally, the recombinant enzyme according to the present invention has a revealed amino acid sequence, and, as an example, the amino acid sequence as shown in SEQ ID NO:2 or 4 which initiates from the N-terminal, as well as homologous ones to it, can be mentioned. Variants having amino acid sequences homologous to the one as shown in SEQ ID NO:2 or 4 can be obtained by replacing one or more bases in SEQ ID NO:2 or 4 with other bases without substantially alternating the inherent activity of the enzyme. Although even when used the same DNA and it also depends on hosts into which the DNA is introduced, as well as on ingredients and components of nutrient culture media used for culturing transformants, and their cultivation temperature and pH, there may be produced modified enzymes which have amino acid sequences similar to that of SEQ ID NO:2 or 4, as well as having the enzymatic activity inherent to the enzyme encoded by the DNA but defective one or more amino acids located near to the N-terminal of the amino acid sequence of SEQ ID NO:2 or 4 and/or having one or more amino acids newly added to the N-terminal by the modification of intracellular enzymes of hosts after the DNA expression. In view of the technical background in the art, the enzyme as referred to in the present invention includes those which have the amino acid sequence corresponding to that of SEQ ID NO:2 or 4, and those which substantially have the amino acid sequence as shown in SEQ ID NO:2 or 4 except that one or more amino acids in the amino acid sequence are defected, newly added to or replaced with other amino acids, as long as they release trehalose form non-reducing saccharides having a trehalose structure as an end unit and having a degree of glucose polymerization of 3 or higher.

In this field, it is known that one or more bases in DNAs can be replaced with other bases by the degeneracy of genetic code without alternating the amino acid sequences encoded by the DNAs. Based on this the DNA according to the present invention includes DNAs which contain the amino acid sequence of SEQ ID NO:1 or 3 and other DNAs, wherein one or more bases are replaced with other bases by degeneracy of genetic code, as long as they encode enzymes having the amino acid sequence as shown in SEQ ID NO:2 or 4 and homologous variants thereof.

According to the today's recombinant DNA technology, the determination of base sequences from the 5'-termini of DNAs define their complementary base sequences. Therefore, the DNA according to the present invention also includes complementary base sequences corresponding to any one of the aforesaid base sequences. Needless to say, one or more bases in the base sequence, which encodes the enzyme or their variants, can be readily replaced with other bases to allow the DNA to actually express the enzyme production in hosts.

The DNA according to the present invention is as described above, and any DNA derived from natural resources and those artificially synthesized can be used in the present invention as long as they have the aforementioned base sequences. The natural resources of the DNA according to the present invention are, for example, microorganisms of the genera Rhizobium, Arthrobacter, Brevibacterium and Micrococcus, i.e. Rhizobium sp. M-11 (FERM BP-4130), Arthrobacter sp. Q36 (FERM BP 4316), *Brevibacterium helovolum* (ATCC 11822) and *Micrococcus roseus* (ATCC 186) from which genes containing the present DNA can be obtained. These microorganisms can be inoculated in nutrient culture media and cultured for about 1–3 days under aerobic conditions, and the resultant cells were collected from the cultures and subjected to ultrasonication or treated with a cell-wall lysis enzyme such as lysozyme or β-glucanase to extract genes containing the present DNA. In this case, a proteolytic enzyme such as protease can be used along with the cell-wall lysis enzyme, and, in the case of treating the cells with ultrasonication, they may be treated in the presence of a surfactant such as sodium dodecyl sulfate (SDS) or treated with freezing- and thawing-methods. The objective DNA is obtainable by treating the resultant with phenol extraction, alcohol sedimentation, centrifugation, protease treatment and/or ribonuclease treatment used in general in the art.

To artificially synthesize the DNA according to the present invention, it can be chemically synthesized by using the base sequence as shown in SEQ ID NO:1 or 3, or can be obtained in plasmid form by inserting a DNA, which encodes the amino acid sequence as shown in SEQ ID NO:2 or 4, into an appropriate self-replicable vector to obtain a recombinant DNA, introducing the recombinant DNA into an appropriate host to obtain a transformant, culturing the transformant, separating the proliferated cells from the resultant culture, and collecting plasmids containing the DNA from the cells.

The present invention further relates to replicable recombinant DNAs which express the production of the enzyme according to the invention when introduced into microorganisms as well as plant- and animal-cells which do not produce the enzyme inherently but are readily proliferative. Such a recombinant DNA, which generally contains the aforesaid DNA and a self-replicable vector, can be prepared by conventional method with a relative easiness when the material DNA is in hand. Examples of such a vector are plasmid vectors such as pBR322, pUC18, Bluescript II SK(+), pUB110, pTZ4, pC194, pHV14, TRp7, TEp7, pBS7, etc.; and phage vectors such as λgt·λC, λgt·λB, p11, φ1, φ105, etc. Among these plasmid- and phage-vectors, pBR322, pUC18, Bluescript II SK(+), λgt·λC and λgt·λB are satisfactorily used in case that the present DNA should be expressed in *Escherichia coli*, while pUB110, pTZ4, pC194, p11, φ1 and φ105 are satisfactorily used to express the DNA in microorganisms of the genus Bacillus. The plasmid vectors pHV14, TRp7, TEp7 and pBS7 are suitably used when the recombinant DNA is allowed to grow in 2 or more hosts.

The methods used to insert the present DNA into such vectors in the present invention may be conventional ones generally used in this field. A gene containing the present DNA and a self-replicable vector are first digested by a restriction enzyme and/or ultrasonic disintegrator, then the resultant DNA fragments and vector fragments are ligated. To digest DNAs and vectors, restriction enzymes which specifically act on nucleotides, particularly, type II restriction enzymes, more particularly, Sau 3AI, Eco RI, Hind III, Bam HI, Sal I, Xba I, Sac I, Pst I, etc., facilitate the ligation of the DNA fragments and vector fragments. The ligation of the DNA fragments and vector fragments is effected by annealing them first if necessary, then subjected to the action of a DNA ligase in vivo or in vitro. The recombinant DNA thus obtained is replicable without substantial limitation by introducing it into appropriate hosts, and culturing the resultant transformants.

The recombinant DNA according to the present invention can be introduced into appropriate host microorganisms including *Escherichia coli* and those of the genus Bacillus as well as actinomyces and yeasts. In the case of using *Escherichia coli* as a host, it can be cultured in the presence of the recombinant DNA and calcium ion, while in the case of using the microorganisms of the genus Bacillus the competent cell method and the colony hybridization method can be employed. Desired transformants can be cloned by the colony hybridization method or by culturing a variety of transformants in nutrient culture media containing non-reducing saccharides having a trehalose structure as an end unit and having a degree of glucose polymerization of 3 or higher, and selecting the objective transformants which release trehalose form the non-reducing saccharides.

The transformants thus obtained extracellularly produce the objective enzyme when cultured in nutrient culture media. Generally, liquid media in general supplemented with carbon sources, nitrogen sources and minerals, and, if necessary, further supplemented with a small amount of amino acids and vitamins can be used as the nutrient culture media. Examples of the carbon sources are saccharides such as starch, starch hydrolysate, glucose, fructose and sucrose. Examples of the nitrogen sources are organic- and inorganic-substances containing nitrogen such as ammonia, ammonium salts, urea, nitrate, peptone, yeast extract, defatted soy been, corn steep liquor and beef extract. Cultures containing the objective enzyme can be prepared by inoculating the transformants into nutrient culture media, and incubating them at a temperature of 25°–65° C. and a pH of 2–8 for about 1–6 days under aerobic aeration-agitation conditions. Such a culture can be used intact as an enzyme preparation, and, usually, it may be disrupted with ultrasonic disintegrator and/or cell-wall lysis enzymes prior to use, followed by separating the enzyme from the intact cells and cell debris by filtration and/or centrifugation, and purifying the enzyme. The methods used for purifying the enzyme in the invention include conventional ones in general. From cultures the intact cells and cell debris are eliminated and subjected to one or more methods such as concentration, salting out, dialysis, separately sedimentation, gel filtration chromatography, ion exchange chromatography, hydrophobic chromatography, affinity chromatography, gel electrophoresis and isoelectric point electrophoresis.

As is described above, the enzyme exerts a distinct activity of forming trehalose from non-reducing saccharides having a trehalose structure as an end unit and having a degree of glucose polymerization of 3 or higher, and such an activity has not yet been found in any conventional enzymes. Therefore, the use of the enzyme facilitates the preparation of trehalose in a relatively-high yield and efficiency from non-reducing saccharides such as α-glucosyltrehalose, α-maltosyltrehalose, α-maltotriosyltrehalose, α-maltotetraosyltrehalose and α-maltopentaosyltrehalose in a considerably-high yield. These non-reducing saccharides can be obtained in a satisfactorily-high yield from starch hydrolysates, which are obtained by treating amylaceous substances such as starch, amylose and amylopectin prepared with acids and/or amylases, by using non-reducing saccharide-forming enzyme as disclosed in Japanese Patent Application No. 349,216/93. Thus, trehalose, whose industrial preparation has been difficult, can be prepared from starch and amylaceous substances as a material with a relative easiness and in a desired amount when the present enzyme and the non-reducing saccharide-forming enzyme, as disclosed in Japanese Patent Application No. 349,216/93, are used in combination.

As described in "Handbook of Amylases and Related Enzymes", 1st edition, edited by The Amylase Research Society of Japan, published by Pergamon Press plc, Oxford, England (1988), α-amylase, maltotetraose-forming amylase, maltopentaose-forming amylase and maltohexaose-forming amylase are especially useful to prepare the reducing amylaceous saccharides used in the invention, and, the use of any one of these amylases readily yields amylaceous saccharide mixtures rich in reducing amylaceous saccharides having a degree of glucose polymerization of 3 or higher in a considerably-high yield. If necessary, the combination use of such an amylase and a starch debranching enzyme such as pullulanase or isoamylase can increase the yield of the reducing amylaceous saccharides usable as a substrate for the non-reducing saccharide-forming enzyme, i.e. the non-reducing saccharides can be obtained by coexisting the non-reducing saccharide-forming enzyme in an aqueous solution containing as a substrate one or more of the reducing amylaceous saccharides in an amount up to a concentration of 50 w/v %, and subjecting the solution to an enzymatic reaction at a temperature of about 40°–55° C. and a pH of about 6–8 until a desired amount of the objective non-reducing saccharides are formed.

Usually, in the present conversion method, the recombinant enzyme according to the present invention is allowed to coexist in the aforesaid aqueous solution containing one or more of the non-reducing amylaceous saccharides, and to enzymatically react with the saccharides while keeping at a prescribed temperature and pH until a desired amount of trehalose is released.

Although the enzymatic reaction proceeds even below a concentration of 0.1 w/v % of a substrate, a higher concentration of 2 w/v %, preferably, 5–50 w/v % of a substrate can be satisfactorily used to apply the present conversion method to an industrial-scale production. The temperature and pH used in the enzymatic reaction are set within the ranges of which do not inactivate the recombinant enzyme and allow the recombinant enzyme to effectively act on substrates, i.e. a temperature up to about 55° C., preferably, a temperature in the range of about 40°–55° C., and a pH of 5–10, preferably, a pH in the range of about 6–8. The amount and reaction time of the present recombinant enzyme are chosen dependently on the enzymatic reaction conditions. The enzymatic reaction effectively converts non-reducing saccharides into saccharide compositions containing trehalose and glucose and/or maltooligosaccharides, and, in the case of using α-maltotriosyltrehalose as a substrate, the conversion rate reaches to approximately 100%. In the case of simultaneously subjecting starch hydrolysates to the action of either of the above amylases together with the non-reducing saccharide-forming enzyme and the present recombinant enzyme, non-reducing saccharides are formed from the hydrolysates while hydrolyzed into glucose and/or maltooligosaccharides, and because of this saccharide compositions with a relatively-high trehalose content can be effectively obtained in a relatively-high yield.

The reaction products obtained by the present conversion reaction can be used intact, and, usually, they are purified prior to use: Insoluble substances are eliminated from the reaction products by filtration and centrifugation, and the resultant solutions are decolored with activated charcoal, desalted and purified on ion exchangers, and concentrated into syrupy products. Dependently on their use, the syrupy products are dried in vacuo and spray-dried into solid products. In order to obtain products which substantially consist of non-reducing saccharides, the above mentioned syrupy products are subjected to one or more methods such as chromatography using an ion exchanger, activated charcoal and silica gel to separate saccharides, separately sedimentation using alcohol and/or acetone, membrane filtration, fermentation by yeasts, and removal and decomposition of reducing saccharides by alkalis. The methods to treat a large amount of reaction mixture are, for example, fixed bed- or pseudomoving bed-ion exchange column chromatography as disclosed in Japanese Patent Laid-Open Nos. 23,799/83 and 72,598/83, and such a method enables an effective industrial-scale production of products with a relatively-high trehalose content.

These trehalose and compositions containing the same have a wide applicability to a variety of products which are apt to be readily damaged by the reducibility of saccharide sweeteners: For example, they can be satisfactorily used as a sweetener, taste-improving agent, quality-improving agent, stabilizer, filler, excipient and adjuvant in food products in general, cosmetics and pharmaceuticals.

The following examples explain the present invention in more detail, and the techniques themselves used in the examples are conventional ones in this field, for example, those described by J. Sumbruck et al. in "Molecular Cloning A Laboratory Manual", 2nd edition, published by Cold Spring Harbor Laboratory Press (1989).

Example 1

Preparation of recombinant DNA containing DNA encoding enzyme M-11 and transformant Example 1-1

Preparation of chromosomal DNA

A seed culture of Rhizobium sp. M-11 was inoculated into bacto nutrient broth medium (pH 7.0), and cultured at 27° C. for 24 hours with a rotary shaker. The cells were separated from the resultant culture by centrifugation, suspended in TES buffer (pH 8.0), admixed with 0.05 w/v % lysozyme, and incubated at 37° C. for 30 min. The resultant was freezed at −80° C. for one hour, admixed with TSS buffer (pH 9.0), heated to 60° C., and further admixed with a mixture solution of TES buffer and phenol, and the resultant solution was chilled with ice, followed by centrifugally collecting the precipitated crude chromosomal DNA. To the supernatant was added 2 fold volumes of cold ethanol, and the reprecipitated crude chromosomal DNA was collected, suspended in SSC buffer (pH 7.1), admixed with 7.5 μg ribonuclease and 125 μg protease, and incubated at 37° C. for one hour. Thereafter, a mixture solution of chloroform and isoamyl alcohol was added to the reaction mixture to extract the objective chromosomal DNA, and admixed with cold ethanol, followed by collecting the formed sediment containing the chromosomal DNA. The purified chromosomal DNA thus obtained was dissolved in SSC buffer (pH 7.1) to give a concentration of about one mg/ml, and the resultant solution was freezed at −80° C.

Example 1-2

Preparation of recombinant DNA pBMU27 and transformant BMU27

About one ml of the purified chromosomal DNA obtained in Example 1-1 was placed in a container, admixed with about 35 units of Sau 3AI, a restriction enzyme, and enzymatically reacted at 37° C. for about 20 min to partially digest the chromosomal DNA, followed by recovering a DNA fragment consisting of about 2,000–6,000 base pairs by means of sucrose density-gradient ultracentrifugation. One μg of Bluescript II SK(+), a plasmid vector, was provided, subjected to the action of Bam HI, a restriction enzyme, to completely digest the plasmid vector, admixed with 10 μg of the DNA fragment and 2 units of T4 DNA ligase, and allowed to stand at 4° C. overnight to ligate the DNA fragment to the vector fragment. To the resultant recombinant DNA was added 30 μl of "Epicurian Coli® XLI-Blue", competent cell commercialized by Toyobo Co., Ltd., Tokyo, Japan, allowed to stand under ice-chilling conditions for 30 min, heated to 42° C., admixed with SOC broth, and incubated at 37° C. for one hour to introduce the recombinant DNA into *Escherichia coli*.

The resultant transformant was inoculated into agar plate (pH 7.0) containing 50 μg/ml of 5-bromo-4-chloro-3-indolyl-β-galactoside, and cultured at 37° C. for 18 hours, followed by placing a nylon film on the agar plate to fix thereon about 6,000 colonies formed on the agar plate. Based on the amino acid sequence located at positions from 8 to 13 as shown in SEQ ID NO:7, i.e. Phe-Asp-Ile-Trp-Ala-Pro, the base sequence of probe 1 represented by 5'-TTYGAYATHTGGGCNCC-3'(SEQ ID NO:15) was chemically synthesized, labelled with $^{32}$P, and hybridized with the colonies of transformants fixed on the nylon film, followed by selecting 14 transformants which exhibited a strong hybridization.

The objective recombinant DNA was selected in usual manner from the 14 transformants, and, in accordance with the method described by E. M. Southern in *Journal of Molecular Biology*, Vol. 98, pp. 503–517 (1975), the recombinant DNA was hybridized with probe 2 having the base sequence as shown in SEQ ID NO:8, which had been chemically synthesized based on the amino acid sequence located at positions from 2 to 6, i.e. Asp-Trp-Ala-Glu-Ala, in SEQ ID NO:8, followed by selecting a recombinant strongly hybridized with the probe 2. The recombinant DNA and transformant thus selected were respectively named "pBMU27" and "BMU27".

The transformant BMU27 was inoculated into L-broth (pH 7.0) containing 100 μg/ml ampicillin, and cultured at 37° C. for 24 hours by a rotary shaker. After completion of the culture, the resultant cells were collected from the culture by centrifugation, and treated with the alkaline method in general to extracellularly extract a recombinant DNA. The extract was in usual manner purified and analyzed to reveal that the recombinant DNA pBMU27 consists of about 5,700 base pairs and has the structure expressed by the restriction map as shown in FIG. 9. It was found that, as shown in FIG. 9, the DNA which consists of 1,767 base pairs for encoding the enzyme M-11 is positioned in the downstream near to the digested site of Eco RV, a restriction enzyme.

Example 1-3

Production of enzyme by transformant BMU27

A liquid nutrient culture medium consisting of 2.0 w/v "PINE-DEX #4", a starch hydrolysate commercialized by Matsutani Chemical Ind., Co., Ltd., Tokyo, Japan, 0.5 w/v % peptone, 0.1 w/v % yeast extract, 0.1 w/v % disodium hydrogen phosphate and 0.1 w/v % potassium dihydrogen phosphate was adjusted to pH 7.0, admixed with 50 μg/ml ampicillin, autoclaved at 120° C. for 20 min, cooled and inoculated with a seed culture of transformant BMU27 obtained in Example 1-2, followed by culturing the transformant at 37° C. for 24 hours by a rotary shaker. The resultant culture was treated with ultrasonic disintegrator to disrupt cells, and the resultant suspension was centrifuged to remove insoluble substances. The supernatant thus obtained was assayed for the enzyme activity to find that one L of the culture yielded about 4,000 units of the enzyme.

As a control, a seed culture of *Escherichia coli* XLI-Blue or Rhizobium sp. M-11 was inoculated in the same fresh preparation of the same liquid nutrient culture medium but free of ampicillin, and, in the case of culturing Rhizobium sp. M-11, it was cultured and treated similarly as above except that the cultivation temperature was set to 30° C. Assaying the resultant activity, one L culture of Rhizobium sp. M-11 yielded about 2,000 units of the enzyme, and the yield was significantly lower than that of transformant BMU27. *Escherichia coli* XLI-Blue used as a host did not form the enzyme.

Thereafter, the enzyme produced by the transformant MBU27 was purified similarly as in Experiment 1-1, and examined on the properties and characters. As a result, it was revealed that it has substantially the same physicochemical properties as enzyme M-11, i.e. it has a molecular weight of about 57,000–68,000 daltons on SDS-PAGE and an isoelectric point of about 3.3–4.6 on isoelectrophoresis. The results indicate that the present enzyme can be prepared by the recombinant DNA technology, and the yield can be significantly increased thereby.

Example 2

Preparation of complementary chain DNA derived from Rhizobium sp. M-11, and determination for its base sequence and amino acid sequence Two μg of the recombinant DNA pBMU27 obtained in Example 1-2 was provided, admixed with 2M aqueous sodium hydroxide solution to effect degeneration, and admixed with an adequate amount of cold ethanol, followed by collecting the formed sediment containing a template DNA and drying the sediment in vacuo. To the template DNA were added 50 pmole/ml of a chemically synthesized primer 1 represented by 5'-GTAAAACGACGGCCAGT-3'(SEQ ID NO:16), 10 µl of 40 mM Tris-HCl buffer (pH 7.5) containing 20 mM magnesium chloride and 20 mM sodium chloride, and the mixture was incubated at 65° C. for 2 min to effect annealing and admixed with 2 µl of an aqueous solution containing dATP, dGTP and dTTP in respective amounts of 7.5 µM, 0.5 µl of [α-$^{32}$P]dCTP (2 mCi/ml), one µl of 0.1 M dithiothreitol, and 2 µl of 1.5 units/ml T7 DNA polymerase, followed by incubating the resultant mixture at 25° C. for 5 min to extend the primer 1 from the 5'-terminus to the 3'-terminus. Thus, a complementary chain DNA was formed.

The reaction product containing the complementary chain DNA was divided into quarters, to each of which 2.5 µl of 50 mM aqueous sodium chloride solution containing 80 µM dNTP and 8 µM ddATP, ddCTP, ddGTP or ddTTP was added, and the resultant mixture was incubated at 37° C. for 5 min, followed by suspending the reaction by the addition of 4 µl of 98 v/v % aqueous formamide solution containing 20 mM EDTA, 0.05 w/v % bromophenol blue, and 0.05 w/v % xylene cyanol. The reaction mixture was heated with a boiling-water bath for 3 min, and a portion of which was placed on a gel containing 6 w/v % polyacrylamide, and electrophoresed by energizing the gel with a constant voltage of about 2,000 volts to separate DNA fragments, followed by fixing the gel in usual manner, drying the gel and subjecting the resultant gel to autoradiography.

Analyses of the DNA fragments separated on the radiogram revealed that the complementary chain DNA contains the base sequence consisting of about 2,161 base pairs as shown in SEQ ID NO:11. An amino acid sequence estimable from the base sequence was as shown in SEQ ID NO:12 and was compared with the amino acid sequence containing the N-terminal or the partial amino acid sequence of enzyme M-11 as shown in SEQ ID NO:5, 7 or 8. As a result, it was found that the amino acid sequence containing the N-terminal of SEQ ID NO:5 corresponds to the amino acid sequence located at positions from 8 to 27 in SEQ ID NO:12, and the partial amino acid sequence of SEQ ID NO:7 or 8 corresponds to the amino acid sequence located at positions from 10 to 30 or at positions from 493 to 509 in SEQ ID NO:12. These results indicate that enzyme M-11 has the amino acid sequence of SEQ ID NO:2, and it is encoded by the DNA having the base sequence as shown in SEQ ID NO:1.

Example 3

Preparation of recombinant DNA, containing DNA derived from arthrobacter sp. Q36, and transformant Example 3-1

Preparation of chromosomal DNA

Similarly as in Example 1-1, a chromosomal DNA was isolated from Arthrobacter sp. Q36, purified and dissolved in SSC buffer (pH 7.1) to give a concentration of about one mg/ml, and the resultant solution was freezed at −80° C. for storage.

Example 3-2

Preparation of recombinant DNA pBRT32 and transformant BRT32

The purified chromosomal DNA obtained in Example 3-1 was partially digested similarly as in Example 1-2, followed by recovering a DNA fragment consisting of about 2,000–6,000 base pairs by sucrose density gradient ultracentrifugation. The DNA fragment was ligated to a lysate of Bluescript II SK(+) which had been treated with Bam HI, and the resultant recombinant DNA was introduced into *Escherichia coli* XLI-Blue. The transformants thus obtained were cultured similarly as in Example 1-2 on agar plates containing 5-bromo-4-chloro-3-indolyl-β-galactoside, and the formed about 5,000 colonies were fixed on a nylon film, while the probe 3 represented by 5'-ATGGGNTGGGAYCCNGC-3' (SEQ ID NO:17) was chemically synthesized based on the amino acid sequence of Met-Gly-Trp-Asp-Pro-Ala located at positions from 5 to 10 in SEQ ID NO:9, labelled with $^{32}$P, and hybridized with transformant colonies which had been fixed on the nylon film, followed by selecting 10 transformants which strongly hybridized with the probe 3.

Similarly as in Example 1-2, the objective recombinant DNA was selected from 10 transformants, and hybridized with probe 4 represented by 5'-TAYGAYGTNTGGGC-3' (SEQ ID NO:18) which had been chemically synthesized based on the amino acid sequence of Tyr-Asp-Val-Trp-Ala located at positions from 8 to 12 in SEQ ID NO:10, followed by selecting a recombinant DNA which strongly hybridized with probe 4. The recombinant DNA and transformant thus selected were respectively named "pBRT32" and "BRT32".

The transformant BRT32 was inoculated into L-broth containing ampicillin, and cultured similarly as in Example 1-2, and the proliferated cells were collected from the resultant culture, and from which a recombinant DNA was extracted, purified and analyzed to reveal that the recombinant DNA pBRT32 consists of about 6,200 base pairs and has the structure of the restriction map as shown in FIG. 10. As shown in FIG. 10, it was revealed that the DNA, which consists of 1,791 base pairs for encoding the DNA of enzyme Q36, is located in the downstream near to the cleavage site of Kpn I.

Example 3-3

Production of enzyme by transformant BRT32

A liquid nutrient culture medium consisting of 2.0 w/v "PINE-DEX #4", a starch hydrolysate commercialized by Matsutani Chemical Ind., Co., Ltd., Tokyo, 0.5 w/v % peptone, 0.1 w/v % yeast extract, 0.1 w/v % disodium hydrogen phosphate and 0.1 w/v potassium dihydrogen phosphate was adjusted to pH 7.0, admixed with 50 µg/ml ampicillin, autoclaved at 120° C. for 20 min, cooled and inoculated with a seed culture of the transformant BRT32 obtained in Example 3-2, followed by culturing the transformant at 37° C. for 24 hours by a rotary shaker. The resultant culture was treated with an ultrasonic disintegrator to disrupt cells, and the resultant suspension was centrifuged to remove insoluble substances. The supernatant thus obtained was assayed for the present enzyme activity to find that one L of the culture yielded about 3,900 units of the enzyme.

As a control, a seed culture of *Escherichia coli* XLI-Blue or Arthrobacter sp. Q36 was inoculated into a fresh preparation of the same liquid nutrient culture medium but free of ampicillin, and, in the case of culturing Arthrobacter sp. Q36, it was cultured and treated similarly as above except that the cultivation temperature was set to 30° C. Assaying the enzyme activity, one L of the culture of Arthrobacter sp. Q36 yielded about 1,800 units of the enzyme, and the yield was significantly lower than that of the transformant BRT32. The *Escherichia coli* XLI-Blue used as a host did not form the enzyme.

Thereafter, the enzyme produced by the transformant BRT32 was purified similarly as in Experiment 1-1, and examined on the properties and characters to reveal that it has substantially the same physicochemical properties as that of enzyme Q36, i.e. it has a molecular weight of about 57,000–68,000 daltons on SDS-PAGE and an isoelectric point of about 3.3–4.6 on isoelectrophoresis. These results indicate that the enzyme can be prepared by the recombinant DNA technology, and the yield can be significantly increased thereby.

Example 4

Preparation of complementary chain DNA derived from Arthrobacter sp. Q36, and determination for its base sequence and amino acid sequence The recombinant DNA pBRT32 obtained in Example 3-2 was similarly treated as in Example 2 to form a template DNA which was then annealed together with the primer 1, followed by allowing T7 DNA polymerase to act on the resultant to extend the primer 1 from the 5'-terminus to the 3'-terminus to obtain a complementary chain DNA. Similarly as in Example 2, the complementary chain DNA was subjected to the dideoxy chain terminator method to analyze DNA fragments which had been isolated on a radiogram. The result revealed that the complementary chain DNA contained a base sequence consisting of 2,056 base pairs as shown in SEQ ID NO:13. An amino acid sequence estimable from the base sequence was as shown in SEQ ID NO:14, and compared with the amino acid sequence containing the N-terminal or the partial amino acid sequence of SEQ ID NO:6, 9 or 10. As a result, it was found that the amino acid sequence of SEQ ID NO:6 corresponds to that located at positions from 2 to 21 in SEQ ID NO:14, and that the partial amino acid sequence in SEQ ID NO:9 or 10 corresponds to that located at positions from 470 to 489 or at positions from 12 to 31 in SEQ ID (NO:14). These results indicate that enzyme Q36 has the amino acid sequence of SEQ ID NO:4, and it is encoded by the DNA having the base sequence as shown in SEQ ID NO:3.

Example 5

Preparation of recombinant enzyme

In 500-ml Erlenmeyer flasks were placed 100 ml aliquots of a liquid nutrient culture medium (pH 7.0) consisting of 2.0 w/v "PINE-DEX #4", a starch hydrolysate commercialized by Matsutani Chemical Ind., Co., Ltd., Tokyo, Japan, 0.5 w/v % peptone, 0.1 w/v % yeast extract, 0.1 w/v % disodium hydrogen phosphate and 0.1 w/v % potassium dihydrogen phosphate, and to each flask was added 50 µg/ml ampicillin and autoclaved at 120° C. for 20 min. Thereafter, the flasks were cooled and inoculated with a seed culture of the transformant BMU27 obtained in Example 1-2, followed by culturing the transformant at 27° C. for 24 hours by a rotary shaker. Apart from this, 18 L of a fresh preparation of the same liquid culture medium was placed in a 30-L jar fermentor, admixed with 50 µg/ml ampicillin, sterilized at 120° C. for 20 min, cooled and inoculated with one v/v % of the seed culture obtained in the above, followed by the culture at 37° C. for 24 hours while keeping the pH at 6–8 under aeration-agitation conditions. The resultant culture was treated with an ultrasonic disintegrator to disrupt cells, and the resultant suspension was centrifuged to remove insoluble substances. The supernatant thus obtained was assayed for the enzyme activity to reveal that one L of the culture yielded about 3,900 units of the enzyme. The supernatant was purified by the method in Experiment 1-1 to obtain an about 67 ml aqueous solution containing an about 165 units/ml of a recombinant enzyme having a specific activity of about 290 units/mg protein.

Example 6

Preparation of recombinant enzyme

Recombinant BRT32 obtained by the method in Experiment 3-2 was cultured similarly as in Example 5, and the resultant culture was treated with an ultrasonic integrator to disrupt cells. The resultant suspension was centrifuged to remove insoluble substances, and the resultant supernatant was assayed for the enzyme activity to have an activity of about 4,000 units per L. The supernatant was purified by the method in Experiment 1-1 to obtain an about 55 ml aqueous solution containing about 200 units/ml of a recombinant enzyme with a specific activity of about 420 units/mg protein.

Example 7

Conversion of non-reducing saccharide by recombinant enzyme

Example 7-1 (a)

Preparation of non-reducing saccharide-forming enzyme

To 500-ml Erlenmeyer flasks were placed 100 ml aliquots of a liquid nutrient culture medium (pH 7.0) consisting of 2.0 w/v maltose, 0.5 w/v % peptone, 0.1 w/v % yeast extract, 0.1 w/v % disodium hydrogen phosphate and 0.1 w/v % potassium dihydrogen phosphate, and the flasks were autoclaved at 120° C. for 20 min. Thereafter, the flasks were cooled and inoculated with a seed culture of Rhizobium sp. M-11, followed by culturing it at 27° C. for 24 hours by a rotary shaker. Apart from this, 20 L of a fresh preparation of the same liquid culture medium was placed in a 30-L jar fermentor, and sterilized, inoculated with one v/v % of the seed culture obtained in the above, followed by the culture at 30° C. and at a pH of 7–8 for 24 hours under aeration-agitation conditions. Thereafter, the resultant culture was treated with an ultrasonic disintegrator to disrupt cells, and the resultant suspension was centrifuged to remove insoluble substances and purified according to the method in Experiment 1-1 to obtain a non-reducing saccharide-forming enzyme having a specific activity of about 195 units/mg protein in a yield of about 220 units per L of the culture.

Throughout the specification the activity of a non-reducing saccharide-forming enzyme is expressed by the value measured on the following assay: Place 4 ml of 50 mM phosphate buffer (pH 7.0) containing 1.25 w/v % maltopentaose in a test tube, add one ml of an enzyme solution to the test tube, and incubate the solution at 40° C. for 60 min to effect enzymatic reaction. Thereafter, the reaction mixture is heated at 100° C. for 10 min to suspend the enzymatic reaction, followed by diluting it with distilled water by 10 times and assaying the reducing activity by the Somogyi-Nelson's method. One unit activity of the non-reducing saccharide-forming enzyme is defined as the amount of enzyme which decreases the reducing power corresponding to one μmol maltopentaose per min under the above conditions.

Example 7-1(b)

Preparation of syrupy product containing trehalose

A potato starch was suspended in water to give a 15 w/w suspension which was then mixed with 0.1 w/w % calcium carbonate. The mixture was adjusted its pH to 6.0, mixed with 0.2 w/w %, d.s.b., of "TERMAMYL 60L", an α-amylase specimen commercialized by Novo Nordisk Bioindustri A/S, Copenhagen, Denmark, and enzymatically reacted at 95° C. for 15 min to effect gelatinization and liquefaction. The liquefied solution was autoclaved at 120° C. for 30 min to inactivate the remaining enzyme, rapidly cooled to 45° C., 1,000 units/g starch, d.s.b., of pullulanase commercialized by Hayashibara Biochemical Laboratories., Inc., Okayama, Japan, 3.4 units/g starch, d.s.b., of the non-reducing saccharide-forming enzyme obtained in Example 7-1(a), and 4.2 units/g starch, d.s.b., of the recombinant enzyme obtained by the method in Example 5, followed the enzymatic reaction for 48 hours. The reaction mixture was heated at 95° C. for 10 min to inactivate the remaining enzyme, cooled, filtered, and, in usual manner, decolored with an activated charcoal, desalted and purified with an ion-exchange resin, and concentrated to obtain a syrupy product with a concentration of about 60 w/w % in a yield of about 92%, d.s.b.

Analysis of the syrup by the method of Experiment 2-1 revealed that it contained 70.2 w/w % trehalose, 2.4 w/w % α-glucosyltrehalose, 3.3 w/w % α-maltosyltrehalose, 0.7 w/w % glucose, 10.1 w/w % maltose, 12.9 w/w % maltotriose, and 0.4 w/w maltooligosaccharides having a degree of glucose polymerization of 4 or higher. The product, having a mild and moderate sweetness as well as an adequate viscosity and moisture-retaining ability, can be satisfactorily used in food products in general, cosmetics and pharmaceuticals as a sweetener, taste-improving agent, quality-improving agent, stabilizer, filler, excipient and adjuvant.

Example 7-1(c)

Preparation of powdery product containing trehalose

To 4 jacketed-stainless steel columns, having a diameter of 5.4 cm and a length of 5 m each was packed homogeneity with "XT-1016 ($Na^+$-form)", a strong-acid cation exchange resin commercialized by Tokyo Organic Chemical Industries, Ltd., Tokyo, Japan, and the columns were cascaded in series to give a total column length of 20 m. The syrupy product obtained in Example 7-1(b) was fed to the columns at a rate of about 5 v/v % against the resin at an inner column temperature of 55° C., and the columns were fed with 55° C. hot water at an SV (space velocity) 0.3 to fractionate saccharides in the syrupy product. Based on the analysis of the saccharide composition of the eluate, fractions rich in trehalose were collected, pooled, concentrated, dried in vacuo and pulverized to obtain a solid product containing about 97 w/w % trehalose in a yield of about 56% against the starting material, d.s.b.

The product, having a mild sweetness and substantially free of reducibility, can be satisfactorily used in food products in general, cosmetics and pharmaceuticals as a sweetener, taste-improving agent, quality-improving agent, stabilizer, filler, excipient and adjuvant.

Example 7-1(d)

Preparation of powdery crystalline trehalose

A portion of the trehalose rich fraction obtained in Example 7-1(c) was concentrated into an about 75 w/w % solution which was then transferred to a crystallizer, admixed with about 2 w/w %, d.s.b., hydrous crystalline trehalose as a seed crystal, and crystallized under gentle stirring conditions to obtain a massecuite with a crystallinity of about 45 w/w %. The massecuite was sprayed downward from a nozzle, equipped at the upper part of a spraying tower at a pressure of about 150 kg/cm$^2$ while about 85° C. hot air was flowing downward from the upper part of the tower to accumulate a crystalline powder on a belt conveyer provided on the basement of the tower, followed by gradually transferring it out of the tower. Thereafter, the powder was transferred to an ageing tower and aged for 10 hours to complete the crystallization and drying while an about 40° C. hot air was blowing to the contents. Thus, a powdery product containing hydrous crystalline trehalose was obtained in a yield of about 90 w/w % against the starting material, d.s.b.

The product, having a substantial non-hygroscopicity and a mild and high-quality sweetness, can be satisfactorily used in food products in general, cosmetics, pharmaceuticals and feeds as a sweetener, taste-improving agent, quality-improving agent, stabilizer, filler, excipient and adjuvant.

Example 8

Conversion of non-reducing saccharide by recombinant enzyme

Potato starch was suspended in water to give a concentration of 6 w/w %, d.s.b., and the suspension was admixed with 500 units/g starch of isoamylase commercialized by Hayashibara Biochemical Laboratories, Inc., Okayama, Japan, and enzymatically reacted for 20 hours. The reaction mixture was adjusted to a pH of 6.5, autoclaved at 120° C. for 10 min to inactivate the remaining enzyme, rapidly cooled to 95° C., admixed with 0.1 w/w % per g starch, d.s.b., of "TERMAMYL 60L", an α-amylase specimen commercialized by Novo Nordisk Bioindustri A/S, Copenhagen, Denmark, and enzymatically reacted for 15 min. The reaction mixture was heated at 130° C. for 30 min to inactivate the remaining enzyme, rapidly cooled to 45° C., admixed with 4.1 units/g starch, d.s.b., of a non-reducing saccharide-forming enzyme obtained by the method in Example 7-1(a), and 4.9 units/g starch, d.s.b., of the present recombinant enzyme obtained by the method in Example 6, and enzymatically reacted for 64 hours. The reaction mixture was heated at 95° C. for 10 min to inactivate the remaining enzyme, rapidly cooled to 55° C., adjusted to pH 5.0, admixed with 10 units/g starch, d.s.b., of "GLUCOZYME", a glucoamylase specimen commercialized by Nagase Biochemicals, Ltd., Kyoto, Japan, and enzymatically reacted for 40 hours. The reaction mixture was heated at 95° C. for 10 min to inactivate the remaining enzyme, cooled, filtered, and, in usual manner, decolored with an activated charcoal, desalted and purified with an ion-exchange resin, and concentrated to obtain an about 60 w/w % syrupy product containing about 80.5 w/w % trehalose, d.s.b. The syrupy product was concentrated into an about 84 w/w % syrup which was then transferred to a crystallizer, admixed with an about 2 w/w % hydrous crystalline trehalose, d.s.b., and crystallized under gentle stirring conditions to obtain a massecuite having a crystallinity of about 45 w/w %. The massecuite was distributed to plastic plain vessels which were then allowed to stand at ambient temperature for 3 days to effect solidification and aging, followed by detaching the resultant blocks from the vessels and pulverizing the blocks with a cutter to obtain a solid product containing hydrous crystalline trehalose in a yield of about 90 w/w % against the material starch, d.s.b.

The product, which is substantially free of hygroscopicity and readily handleable, can be arbitrarily used in food products in general, cosmetics, pharmaceuticals as a sweetening agent, taste-improving agent, quality-improving agent, stabilizer, filler, excipient and adjuvant.

Example 9

Conversion of non-reducing saccharide by recombinant enzyme

Potato starch was suspended in water to give a concentration of 6 w/w %, d.s.b., and the suspension was admixed with 0.01 w/w % "NEO-SPITASE", α-amylase commercialized by Nagase Biochemicals, Ltd., Kyoto, Japan, adjusted to pH 6.2, and enzymatically reacted at 85°–90° C. for 20 min to gelatinize and liquefy the starch. The liquefied starch was heated at 120° C. for 10 min to inactivate the remaining enzyme, rapidly cooled to 45° C., admixed with 500 units/g starch, d.s.b., of isoamylase commercialized by Hayashibara Biochemical Laboratories, Inc., Okayama, Japan, 3.2 units/g starch, d.s.b., of a non-reducing saccharide-forming enzyme obtained by the method in Example 7-1(a), and 5.0 units/g starch, d.s.b., of the present recombinant enzyme obtained by the method in Example 5, and enzymatically reacted for 48 hours. The reaction mixture was heated at 95° C. for 10 min to inactivate the remaining enzyme, rapidly cooled to 55° C., adjusted to pH 5.0, admixed with 10 units/g starch, d.s.b., of "GLUCOZYME", glucoamylase commercialized by Nagase Biochemicals Ltd., Kyoto, Japan, and enzymatically reacted for 40 hours. The reaction mixture was heated at 95° C. for 10 min to inactivate the remaining enzyme, rapidly cooled, filtered, and, in usual manner, decolored with an activated charcoal, desalted and purified with an ion-exchanGe resin, and concentrated to Give a concentration of about 60 w/w %, d.s.b., to obtain a syrupy product containing 78.3 w/w % trehalose, d.s.b. The syrupy product was fractionated similarly as in Example 7-1(c) except for using "CG6000(Na$^+$)", a stronG-acid cation exchange resin commercialized by Japan Organo, Co., Ltd., Tokyo, Japan, to obtain a fraction containing abut 95 w/w % trehalose, d.s.b. The fraction was concentrated to give a concentration of about 75 w/w %, d.s.b., and, similarly as in Example 8, crystallized, and the resultant massecuite in the form of block was pulverized to obtain a powdery product containing hydrous crystalline trehalose in a yield of about 70 w/w % against the material starch, d.s.b.

The product, which is substantially free of hygroscopicity and readily handleable, can be arbitrarily used in food products in general, cosmetics, pharmaceuticals as a sweetening agent, taste-improving agent, quality-improving agent, stabilizer, filler, excipient and adjuvant.

As is described above, the present invention is based on the finding that a novel enzyme which releases trehalose from non-reducing saccharides having a trehalose structure as an end unit and having a degree of glucose polymerization of 3 or higher. The present invention is to explore a way to produce the enzyme in a relatively-large scale and in a considerably-high yield. The enzyme produced by the transformant according to the present invention is the one characterized by its revealed total amino acid sequence, and because of this it can be used for the preparations of trehalose which is premised on being used in food products without fear of causing side effects.

Therefore, the present invention is an useful invention which exerts the aforesaid significant action and effect as well as giving a great contribution to this field.

We claim:

1. A DNA molecule, which is derived from a microorganism selected from the genera consisting of Rhizobium, Arthrobacter, Brevibacterium, and Micrococcus, encoding an enzyme which releases trehalose from a non-reducing saccharide having a trehalose structure as an end unit and having a degree of glucose polymerization of 3 or higher.

2. The DNA molecule as claimed in claim 1, wherein said enzyme has the following physiocochemical properties of:

(1) Molecular weight

About 57,000–68,000 daltons on sodium dodecyl sulfate polyacrylamide gel electrophoresis (SDS-PAGE); and (2) Isoelectric point (pI)

About 3.3–4.6 on isoelectrophoresis.

3. The DNA molecule as claimed in claim 1, wherein said enzyme has an amino acid sequence selected from the group consisting of SEQ ID NOs:2 and 4 that initiate from the N-terminal, and homologous amino acid sequences to these amino acid sequences.

4. The DNA molecule as claimed in claim 1, which has a base sequence selected from the group consisting of SEQ ID NOs:1 and 3 that initiate from the 5'-terminus, homologous base sequences to the base sequences, and complementary base sequences to these base sequences: SEQ ID NO:1.

5. The DNA as claimed in claim 4, wherein one or more bases in SEQ ID NOs:1 and 3 are replaced with other bases by means of degeneracy of genetic code without altering their corresponding amino acid sequences of SEQ ID NOs:2 and 4.

6. The DNA as claimed in claim 1, which has a base sequence selected from the group consisting of SEQ ID NOs:11 and 13.

7. A replicable recombinant DNA molecule containing the DNA as claimed in claim 1 and a self-replicable vector.

8. The replicable recombinant DNA molecule as claimed in claim 7, wherein said self-replicable vector is a plasmid vector Bluescript II SK(+).

9. The replicable recombinant DNA molecule as claimed in claim 7, wherein the DNA has a base sequence selected from the group consisting of SEQ ID NOs:1 and 3 that initiate from the 5'-terminus, homologous base sequences to the base sequences, and complementary base sequences to these base sequences.

10. The replicable recombinant DNA molecule as claimed in claim 9, wherein the DNA is obtained by replacing one or more bases in SEQ ID NOs:1 and 3 with other bases by means of degeneracy of genetic code without altering their corresponding amino acid sequences SEQ ID NOs:2 and 4.

11. The replicable recombinant DNA molecule as claimed in claim 7, wherein the DNA has a base sequence selected from the group consisting of SEQ ID NOs:11 and 13.

12. A transformant obtained by introducing into a host cell a replicable recombinant DNA which comprises a self-replicable vector and the DNA molecule as claimed in claim 1.

13. The transformant as claimed in claim 12, which produces an enzyme that releases trehalose from a non-reducing saccharide having a trehalose structure as an end unit and having a degree of glucose polymerization of 3 or higher.

14. The transformant as claimed in claim 13, wherein said enzyme has the following physicochemical properties of:

(1) Molecular weight

About 57,000–68,000 daltons on sodium dodecyl sulfate polyacrylamide gel electrophoresis (SDS-PAGE); and (2) Isoelectric point (pI)

About 3.3–4.6 on isoelectrophoresis.

15. The transformant as claimed in claim 13, wherein said enzyme has an amino acid sequence selected from the group consisting of SEQ ID NOs:2 and 4 that initiate from the N-terminal, and homologous amino acid sequences to these amino acid sequences.

16. The tranformant as claimed in claim 12, wherein the DNA molecule has a base sequence selected from the group consisting of SEQ ID NOs:1 and 3 that initiate from the 5'-terminus, homologous base sequences to the base sequences, and complementary base sequences to these base sequences:

17. The transformant as claimed in claim 12, wherein the DNA molecule has a base sequence selected from the group consisting of SEQ ID NOs:1 and 3 wherein one or more bases in SEQ ID NOs:1 and 3 are replaced with other bases by means of degeneracy of genetic code without altering their corresponding amino acid sequences of SEQ ID NOs:2 and 4.

18. The transformant as claimed in claim 12, wherein the DNA molecule has a base sequence selected from the group consisting of SEQ ID NOs:11 and 13.

19. The transformant as claimed in claim 12, wherein said host cell is of the spices *Escherichia coli*.

20. A process for producing a recombinant enzyme, which comprises culturing the transformant as claimed in claim 12 to produce a recombinant enzyme which releases trehalose from a non-reducing saccharide having a trehalose structure as an end unit and having a degree of glucose polymerization of 3 or higher, and collecting the recombinant enzyme from the resultant culture.

21. The process as claimed in claim 20, wherein the recombinant enzyme is encoded by a base sequence selected from the group consisting of SEQ ID NOs:1 and 3 that initiate from the 5'-terminus, homologous base sequences to the base sequences, and complementary base sequence to these base sequences.

22. The process as claimed in claim 20, wherein the recombinant enzyme is encoded by a base sequence selected from the group consisting of SEQ ID NOs:1 and 3 wherein one or more bases are replaced with other bases by means of degeneracy of genetic code without altering their corresponding amino acid sequences of SEQ ID NOs:2 and 4.

23. The process as claimed in claim 20, wherein the recombinant enzyme is encoded by a base sequence selected from the group consisting of SEQ ID NOs:11 and 13.

24. The process as claimed in claim 20, wherein the transformant is inoculated into a liquid culture medium having a pH of 2–8, and cultured at a temperature of 25°–65° C. for about 1–6 days.

25. The process as claimed in claim 20, wherein the collecting step of the recombinant enzyme is effected by one or more methods selected from the group consisting of centrifugation, filtration, concentration, salting out, dialysis, ion-exchange chromatography, gel filtration chromatography, hydrophobic chromatography, affinity chromatography, gel electrophoresis and isoelectrophoresis.

26. The process as claimed in claim 20, wherein the recombinant enzyme has the following physicochemical properties of:

(1) Molecular weight

About 57,000–68,000 daltons on sodium dodecyl sulfate polyacrylamide gel electrophoresis (SDS-PAGE); and (2) Isoelectric point (pI)

About 3.3–4.6 on isoelectrophoresis.

* * * * *